(12) United States Patent
Hu et al.

(10) Patent No.: US 11,813,326 B2
(45) Date of Patent: Nov. 14, 2023

(54) CELL-ASSOCIATING IMMUNOLOGIC ADJUVANTS FOR TREATMENT ENHANCEMENT

(71) Applicant: ACADEMIA SINICA, Taipei (TW)

(72) Inventors: Che-Ming Jack Hu, Taipei (TW); Saborni Chattopadhyay, Taipei (TW)

(73) Assignee: ACADEMIA SINICA, Taipei (TW)

( * ) Notice: Subject to any disclaimer, the term of this patent is extended or adjusted under 35 U.S.C. 154(b) by 173 days.

(21) Appl. No.: 16/959,758

(22) PCT Filed: Jan. 3, 2019

(86) PCT No.: PCT/US2019/012138
§ 371 (c)(1),
(2) Date: Jul. 2, 2020

(87) PCT Pub. No.: WO2019/136118
PCT Pub. Date: Jul. 11, 2019

(65) Prior Publication Data
US 2021/0361765 A1    Nov. 25, 2021

Related U.S. Application Data

(60) Provisional application No. 62/613,574, filed on Jan. 4, 2018.

(51) Int. Cl.
*A61K 39/39* (2006.01)
*A61K 9/51* (2006.01)
*A61K 39/00* (2006.01)

(52) U.S. Cl.
CPC ......... *A61K 39/39* (2013.01); *A61K 9/5153* (2013.01); *A61K 2039/55561* (2013.01)

(58) Field of Classification Search
CPC ........ A61K 39/39; A61K 9/5153; A61K 9/14; A61K 9/16
See application file for complete search history.

(56) References Cited

U.S. PATENT DOCUMENTS

2008/0207657 A1 *  8/2008  Black ................. A61P 35/04
                                                        514/275
2010/0112011 A1 *  5/2010  Friedberg ........... A61K 39/0011
                                                        424/277.1
(Continued)

FOREIGN PATENT DOCUMENTS

WO   WO 2017/023749 A     2/2017
WO   WO-2017151922 A1 *  9/2017  ....... A61K 39/00119
WO   WO-2017165506 A1 *  9/2017  ........... A61K 31/708

OTHER PUBLICATIONS

Hiroko Miyabe, Mamoru Hyodo, Takashi Nakamura, Yusuke Sato, Yoshihiro Hayakawa, Hideyoshi Harashima. "A new adjuvant delivery system 'cyclic di-GMP/YSK05 liposome' for cancer immunotherapy." Journal of Controlled Release, vol. 184 (2014), pp. 20-27. (Year: 2014).*

(Continued)

*Primary Examiner* — Isaac Shomer
(74) *Attorney, Agent, or Firm* — Birch, Stewart, Kolasch & Birch, LLP

(57) ABSTRACT

This disclosure provides treatment kit that are capable of modulating the immune response. The treatment kit may also be used enhance the immunogenicity of antigens released from cell debris. Also provided are methods of using the treatment kit.

19 Claims, 32 Drawing Sheets

Specification includes a Sequence Listing.

(56) References Cited

U.S. PATENT DOCUMENTS

| | | | | |
|---|---|---|---|---|
| 2013/0315831 A1* | 11/2013 | Shi | ...................... | A61K 9/5073 |
| | | | | 424/9.1 |
| 2015/0056224 A1* | 2/2015 | Dubensky, Jr. | ........ | C07H 21/02 |
| | | | | 514/48 |
| 2015/0086611 A1* | 3/2015 | Lee | ...................... | A61K 47/42 |
| | | | | 604/20 |
| 2015/0343056 A1* | 12/2015 | Chen | ...................... | A61P 43/00 |
| | | | | 435/7.1 |
| 2016/0362441 A1* | 12/2016 | Vernejoul | .......... | A61K 31/7084 |
| 2018/0244712 A1* | 8/2018 | Altman | .................. | C07H 21/00 |

OTHER PUBLICATIONS

Takashi Nakamura et al. "Incorporation of polyinosine-polycytidylic acid enhances cytotoxic T cell activity and antitumor effects by octaarginine-modified liposomes encapsulating antigen, but not by octaarginine-modified antigen complex." International Journal of Pharmaceutics, vol. 441, pp. 476-481. (Year: 2013).*

Takashi Nakamura et al. "Liposomes loaded with a STING pathway ligand, cyclic di-GMP, enhance cancer immunotherapy against metastatic melanoma." Journal of Controlled Release 216 (2015), pp. 149-157. (Year: 2015).*

Martin Kreutz, Paul J. Tacken, and Carl G. Figdor. "Targeting dendritic cells—why bother?" Blood, vol. 121 No. 15, Apr. 11, 2013, pp. 2836-2844. (Year: 2013).*

David R. Khan, Evonne M. Rezler, Janelle Lauer-Fields and Gregg B. Fields. "Effects of Drug Hydrophobicity on Liposomal Stability" Chemical Biology & Drug Design, vol. 71, 2008, pp. 3-7. (Year: 2008).*

Priya Luthra et al. "Topoisomerase II Inhibitors Induce DNA Damage-Dependent Interferon Responses Circumventing Ebola Virus Immune Evasion." mBio, vol. 8 Issue 2, Article e00368-17, Mar./Apr. 2017, pp. 1-19. (Year: 2017).*

International Search Report, issued in PCT/US2019/012138, dated Jul. 24, 2019.

Liu et al., "Coordinating antigen cytosolic delivery and danger signaling to program potent cross-priming by micelle-based nanovaccine", Cell Discovery, 2017, 3, 17007, total 14 pages.

Roy et al., "Nanoparticle mediated co-delivery of paclitaxel and a TLR-4 agonist results in tumor regression and enhanced immune response in the tumor microenvironment of a mouse model", International Journal of Pharmaceutics, 2013, vol. 445, pp. 171-180.

Written Opinion of the International Searching Authority, issued in PCT/US2019/012138, dated Jul. 24, 2019.

* cited by examiner

SEQUENCE LISTING

```
<160> NUMBER OF SEQ ID NOS: 6

<210> SEQ ID NO 1
<211> LENGTH: 13
<212> TYPE: PRT
<213> ORGANISM: Artificial Sequence
<220> FEATURE:
<223> OTHER INFORMATION: HIV-1 TAT peptide

<400> SEQUENCE: 1

Gly Arg Lys Lys Arg Arg Gln Arg Arg Arg Pro Pro Gln
1               5                   10

<210> SEQ ID NO 2
<211> LENGTH: 16
<212> TYPE: PRT
<213> ORGANISM: Artificial Sequence
<220> FEATURE:
<223> OTHER INFORMATION: penetratin

<400> SEQUENCE: 2

Arg Gln Ile Lys Ile Trp Phe Gln Asn Arg Arg Met Lys Trp Lys Lys
1               5                   10                  15

<210> SEQ ID NO 3
<211> LENGTH: 4
<212> TYPE: PRT
<213> ORGANISM: Artificial Sequence
<220> FEATURE:
<223> OTHER INFORMATION: polyarginines
<220> FEATURE:
<221> NAME/KEY: REPEAT
<222> LOCATION: (1)..(1)
<223> OTHER INFORMATION: polyarginines comprising R repeated n times

<400> SEQUENCE: 3

Arg Arg Arg Arg
1

<210> SEQ ID NO 4
<211> LENGTH: 26
<212> TYPE: PRT
<213> ORGANISM: Artificial Sequence
```

```
<220> FEATURE:
<223> OTHER INFORMATION: transportan

<400> SEQUENCE: 4

Gly Trp Thr Leu Asn Ser Ala Gly Tyr Leu Leu Gly Ile Asn Leu Lys
1               5                   10                  15

Ala Leu Ala Ala Leu Ala Lys Lys Ile Leu
            20                  25

<210> SEQ ID NO 5
<211> LENGTH: 8
<212> TYPE: PRT
<213> ORGANISM: Artificial Sequence
<220> FEATURE:
<223> OTHER INFORMATION: ovalbumin peptide OTI

<400> SEQUENCE: 5

Ser Ile Ile Asn Phe Glu Lys Leu
1               5

<210> SEQ ID NO 6
<211> LENGTH: 9
<212> TYPE: PRT
<213> ORGANISM: Artificial Sequence
<220> FEATURE:
<223> OTHER INFORMATION: ovalbumin peptide OTII

<400> SEQUENCE: 6

Ala Ala His Ala Glu Ile Asn Glu Ala
1               5
```

CELL-ASSOCIATING IMMUNOLOGIC ADJUVANTS FOR TREATMENT ENHANCEMENT

CROSS-REFERENCE TO RELATED APPLICATION

This application is the National Phase of PCT International Application No. PCT/US2019/012138, filed on Jan. 3, 2019, which claims priority under 35 U.S.C. 119(e) to U.S. Provisional Application No. 62/613,574, filed on Jan. 4, 2018, all of which are hereby expressly incorporated by reference into the present application.

FIELD OF INVENTION

This present disclosure relates to a treatment kit and methods for using the same.

BACKGROUND OF THE INVENTION

Effective immune potentiation against antigenic targets hinges on the coordinated presentation of antigens and immune-stimulatory signals. Activation of innate immune signals via agonists of the pathogen recognition receptors trigger the secretion of specific cytokine milieu, which in turn shape the adaptive immunity against the antigen target. This mechanism is frequently exploited in vaccine designs as vaccine antigens are often formulated with immunologic adjuvants to enhance immune potentiation. Once the immune system is primed against a foreign antigen, the adaptive immune cells work to recognize and eliminate similarly suspicious cells, while retaining a memory of the same antigen, allowing a quicker, more potent assault upon recurrence of infection[1].

The role of adaptive immunity is increasingly recognized in the battle against malignant cells, i.e. cancer, as immune cells such as cytotoxic T lymphocytes can facilitate eradication of these cellular targets. Tumor cells frequently express tumor-associated antigens, which serve as targets for vaccine development. Recent studies have shown that by formulating tumor-associated antigens with immunologic adjuvants, the resulting vaccine formulations can enhance tumor-specific immunity and facilitate better cancer treatment outcomes[2]. These cancer vaccine formulations require genomic analysis of tumor samples for the identification of specific peptide sequences, which can then be synthesized for vaccine development.

Alternatively, whole cell-based tumor vaccines have also been developed by extracting patient cancer cell samples or using allogeneic cancer cells. In these approaches, tumor cell derivatives are formulated with adjuvants exogenously prior to administration. The adjuvant mixtures may then increase the immunogenicity of tumor-associated antigens in the tumor cell derivatives. In one example, dead cancer cells were functionalized with adjuvant-nanoparticles ex vivo to vaccinate against subcutaneous tumors[3]. The platform in itself has a 30% efficiency that can be increased up to 78% when combined with an immune check-point blocker therapy. In another example, allogenic cancer cells were formulated with a STING agonist ex vivo as a vaccine formulation[4]. The formulation, known as STING-VAX, was able to elicit anti-tumor immunity upon administration in animal models.

The induction of endogenous immune-stimulatory molecules has also been identified as an important factor behind successful cancer treatment. Several cancer treatments, including several types of chemotherapy, radiation, and oncolytic viruses, have been demonstrated to induce cellular stress in cancer cell and trigger immunogenic cell death (ICD). This type of cell death is associated with endogenous release of danger associated molecular patterns (DAMPs), which consist of a combination of peptides, proteins, or nucleic acids originated from the dying cells[5]. Together with the antigenic materials from the dying cells, these endogenous danger signals promote antigen-specific adaptive immunity. Mounting evidence suggests that this innate mechanism of co-displaying antigens and immune-stimulatory molecules is critical to containing disease progression in patients affected by a plethora of neoplasms[6]. It is thus conceivable that such mechanism may be enhanced with the aid of exogenous adjuvants, which may further amplify the immune response to released tumor antigens following cancer cell death.

SUMMARY OF THE INVENTION

In the present application, we develop immunologic adjuvants that can be associated with cells and demonstrate its use to enhance the immunogenicity of released antigens from cells during treatment. As shown in FIG. 1, by associating exogenous immunologic adjuvants with functionalities that can associate with cancer cells—such as through the means of cellular internationalization, membrane association, or surface ligand binding—the adjuvants can flag the cellular targets for immune potentiation. Subsequent treatment that induces release of cellular debris, vesicles, and antigens would thus trigger immune responses regardless of whether the treatment itself triggers endogenous danger signals. This application thus concerns about both functionalization of immunologic adjuvants and treatment modalities associated with the functionalized adjuvants. The claimed invention may be applied to any pathogenic cells beyond cancers. Specifically, an immunologic adjuvants are designed to associate with malignant cells, which can be through either intracellular (cellular internationalization) or extracellular means (membrane-tethering or surface ligand binding). Malignant cells treated with the functionalized adjuvants are then induced to release cellular debris, vesicles, and antigens. Induction of antigen release can be triggered by any stimuli know in the art. For instance, the stimuli may at least comprise chemical agents, biological agents, light, or mechanical stimuli.

In the scope of present invention, a treatment modality for pathogenic cell is provided where the diseased cells are first administered with exogenous adjuvants. The exogenous adjuvants can be associated with the cells as follows: (1) an adjuvant formulation that allows intracellular delivery of the desired adjuvants, e.g. nanoparticles, exosomes, engineered cell penetrating peptides etc.; (2) an adjuvant formulation that can be partitioned into the cell membrane, e.g. adjuvant with lipophilic linkers, amphiphilic adjuvants etc.; and (3) an adjuvant formulation that has binding affinity to cell surface moieties and capable of physically associating with cell membrane moieties, e.g. adjuvant coupled with antibody, adjuvant coupled with aptamers, adjuvant-sugar formulations etc.

Once the adjuvant is associated with the infected cell, the cell is then treated with a vesiculating, antigen-releasing stimuli that include but not limited to chemotherapy drugs, biologic agents, irradiation, photolytic agents, mechanical disruption etc. The regimen facilitates the production of co-localized antigen with exogenous adjuvants in vivo. In principle, the cell-associating immunogenic adjuvants can be applied to complement any existing or emerging treatment modalities aimed at eradicating pathogenic cells.

In one aspect, provided herein is a treatment kit, comprising: an immunologic adjuvant formulation capable of physically associating with cells; and a means for inducing antigen release from a cell.

In another aspect, provided herein is a method of treating a disease, comprising: administering to a subject in need thereof an immunologic adjuvant formulation capable of physically associating with cells; and administering to the subject in need thereof a means for inducing antigen release from a cell.

Preferably, the immunologic adjuvant formulation may comprise a polymeric nanoparticle encapsulating an adjuvant, and the polymeric nanoparticle may further comprise: a polymeric shell impermeable to water, and one or more aqueous cores enclosed by the polymeric shell.

Preferably, the polymeric shell may have a thickness less than 25 nm and the polymeric nanoparticle has an outer diameter of 30-600 nm.

Preferably, the means for inducing antigen release from a cell may be encapsulated in the polymeric nanoparticle.

Preferably, the immunologic adjuvant formulation may comprise MPLA, CpG, poly(I:C), or variants of cyclic-dinucleotides.

Preferably, the immunologic adjuvant formulation may comprise an agonist to a cytoplasmic pattern recognition receptor or a stimulator of interferon genes (STING).

Preferably, the agonist may be cyclic di-GMP or cyclic GAMP.

Preferably, the immunologic adjuvant formulation comprises an adjuvant conjugated to a small molecule, a peptide, an antibody, an aptamer, a sugar moiety, a polymer or a combination thereof for recognizing and binding to a moiety on a cell surface.

Preferably, the antibody may be an immunoglobulin molecule, an Fv, a disulfide linked Fv, a monoclonal antibody, a scFv, a chimeric antibody, a single domain antibody, a CDR-grafted antibody, a diabody, a humanized antibody, a multispecific antibody, an Fab, a dual specific antibody, an Fab' fragment, a bispecific antibody, an F(ab')2 fragment, a bivalent fragment comprising two Fab fragments linked by a disulfide bridge at the hinge region; a Fd fragment consisting of the VH and CH1 domains; a Fv fragment consisting of the VL and VH domains of a single arm of an antibody, a dAb fragment, an isolated complementarity determining region (CDR), or a single chain antibody.

Preferably, the immunologic adjuvant formulation may comprises an adjuvant conjugated to a molecule capable of tethering to a cell membrane.

Preferably, the molecule may be lipophilic or amphiphilic.

Preferably, the lipophilic molecule may comprise fatty acid chains, cholesterol, or phospholipids.

Preferably, the amphiphilic molecule may comprises lipid-PEG conjugates.

Preferably, the immunologic adjuvant formulation may comprises an adjuvant formulated with nanoparticulates or cell penetrating peptides for intracellular delivery.

Preferably, the cell penetrating peptides may comprise HIV-1 TAT peptide (GRKKRRORRRPPQ, SEQ ID NO: 1), penetratin (RQIKIWFQNRRMKWKK, SEQ ID NO: 2), polyarginines (Rn, SEQ ID NO: 3), or transportan (GWTLNSAGYLLGINLKALAALAKKIL, SEQ ID NO: 4).

Preferably, the means for inducing antigen release may comprise chemical agents, biological agents, irradiation, photolytic agents, mechanical disruptions, or a combination thereof.

Preferably, the chemical agents may comprise a cytotoxic agent.

Preferably, the cytotoxic agent may comprise Monomethyl auristatin E (MMAE), Monomethyl auristatin F (MMAF), mertansine (DM1), anthracycline, pyrrolobenzodiazepine, α-amanitin, tubulysin, benzodiazepine, erlotinib, bortezomib, fulvestrant, sunitinib, letrozole, imatinib mesylate, PTK787/ZK 222584, oxaliplatin, leucovorin, rapamycin, lapatinib, lonafarnib (SARASAR®, SCH 66336), sorafenib, gefitinib, AG1478, AG1571, alkylating agent; alkyl sulfonate; aziridines; ethylenimine; methylamelamine; acetogenins; camptothecin; bryostatin; callystatin; CC-1065; cryptophycins; dolastatin; duocarmycin; eleutherobin; pancratistatin; sarcodictyin; spongistatin; chlorambucil; chlornaphazine; cholophosphamide; estramustine; ifosfamide; mechlorethamine; mechlorethamine oxide hydrochloride; melphalan; novembichin; phenesterine; prednimustine; trofosfamide; uracil mustard; carmustine; chlorozotocin; fotemustine; lomustine; nimustine; ranimustine; calicheamicin; dynemicin; clodronate; esperamicin; neocarzinostatin chromophore; aclacinomysins; actinomycin; authramycin; azaserine; bleomycins; cactinomycin; carabicin; caminomycin; carzinophilin; chromomycinis; dactinomycin; daunorubicin; detorubicin; 6-diazo-5-oxo-L-norleucine; doxorubicin; epirubicin; esorubicin; idarubicin; marcellomycin; mitomycin; mycophenolic acid; nogalamycin; olivomycins; peplomycin; potfiromycin; puromycin; quelamycin; rodorubicin; streptonigrin; streptozocin, tubercidin, ubenimex, zinostatin, zorubicin; methotrexate; 5-fluorouracil (5-FU); denopterin; pteropterin; trimetrexate; fludarabine; 6-mercaptopurine; thiamiprine; thioguanine; ancitabine; azacitidine; 6-azauridine; carmofur; cytarabine; dideoxyuridine; doxifluridine; enocitabine; floxuridine; calusterone; dromostanolone propionate; epitiostanol; mepitiostane; testolactone; aminoglutethimide; mitotane; trilostane; frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; epothilone; etoglucid; gallium nitrate; hydroxyurea; lentinan; lonidainine; maytansine; ansamitocins; mitoguazone; mitoxantrone; mopidanmol; nitraerine; pentostatin; phenamet; piraubicin; losoxantrone; podophyllinic acid; 2-ethylhydrazide; procarbazine; razoxane; rhizoxin; sizofiran; spirogermanium; tenuazonic acid; triaziquone; 2,2',2''-trichlorotriethylamine; trichothecene; urethan; vindesine; dacarbazine; mannomustine; mitobronitol; mitolactol; pipobroman; gacytosine; arabinoside; cyclophosphamide; thiotepa; taxoid; paclitaxel; doxetaxel; chloranbucil; gemcitabine; 6-thioguanine; mercaptopurine; methotrexate; cisplatin; carboplatin; vinblastine; platinum; etoposide; ifosfamide; mitoxantrone; vincristine; vinorelbine; novantrone; teniposide; edatrexate; daunomycin; aminopterin; xeloda; ibandronate; topoisomerase inhibitor; difluoromethylornithine (DMFO); retinoid; capecitabine; or a combination thereof.

Preferably, the photolytic agents comprises Photofrin, Laserphyrin, Aminolevulinic acid (ALA), Silicon Phthalocyanine Pc 4, m-tetrahydroxyphenylchlorin (mTHPC), chlorin e6 (Ce6), Allumera, Levulan, Foscan, Metvix, Hexvix, Photochlor, Photosens, Photrex, Lumacan, Visonac, Amphinex, Verteporfin, Purlytin, ATMPn, Zinc phthalocyanine (ZnPc), Protoporphyrin IX (PpIX), Pyropheophorbidea (PPa), Pheophorbide a (PhA), or a combination thereof.

Preferably, the method may further comprise: encapsulating an adjuvant in a polymeric nanoparticle. The polymeric nanoparticle may comprise: a polymeric shell impermeable to water, and one or more aqueous cores enclosed by the polymeric shell.

Preferably, the means for inducing antigen release may be administered to the subject in need before or after administration of the immunologic adjuvant formulation.

Preferably, the means for inducing antigen release may be administered to the subject in need at the same time as the immunologic adjuvant formulation.

Preferably, the method may further comprise: encapsulating the means for inducing antigen release from a cell in the immunologic adjuvant formulation.

Preferably, the method may further comprise: conjugating an adjuvant with a small molecule, a peptide, an antibody, an aptamer, a sugar moiety, a polymer or a combination thereof recognizing and binding to a moiety on a cell surface to form the immunologic adjuvant formulation.

Preferably, the method may further comprise: conjugating an adjuvant with a molecule capable of tethering to a cell membrane.

Preferably, the method may further comprise: formulating an adjuvant with nanoparticulates or cell penetrating peptides for intracellular delivery.

Preferably, the step of administering to the subject may be by at least one mode selected from the group consisting of parenteral, subcutaneous, intramuscular, intravenous, intraarticular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, and transdermal.

Preferably, the disease may be cardiovascular disease, cancer, autoimmune disease, or infection.

DETAILED DESCRIPTION

Figure 1:
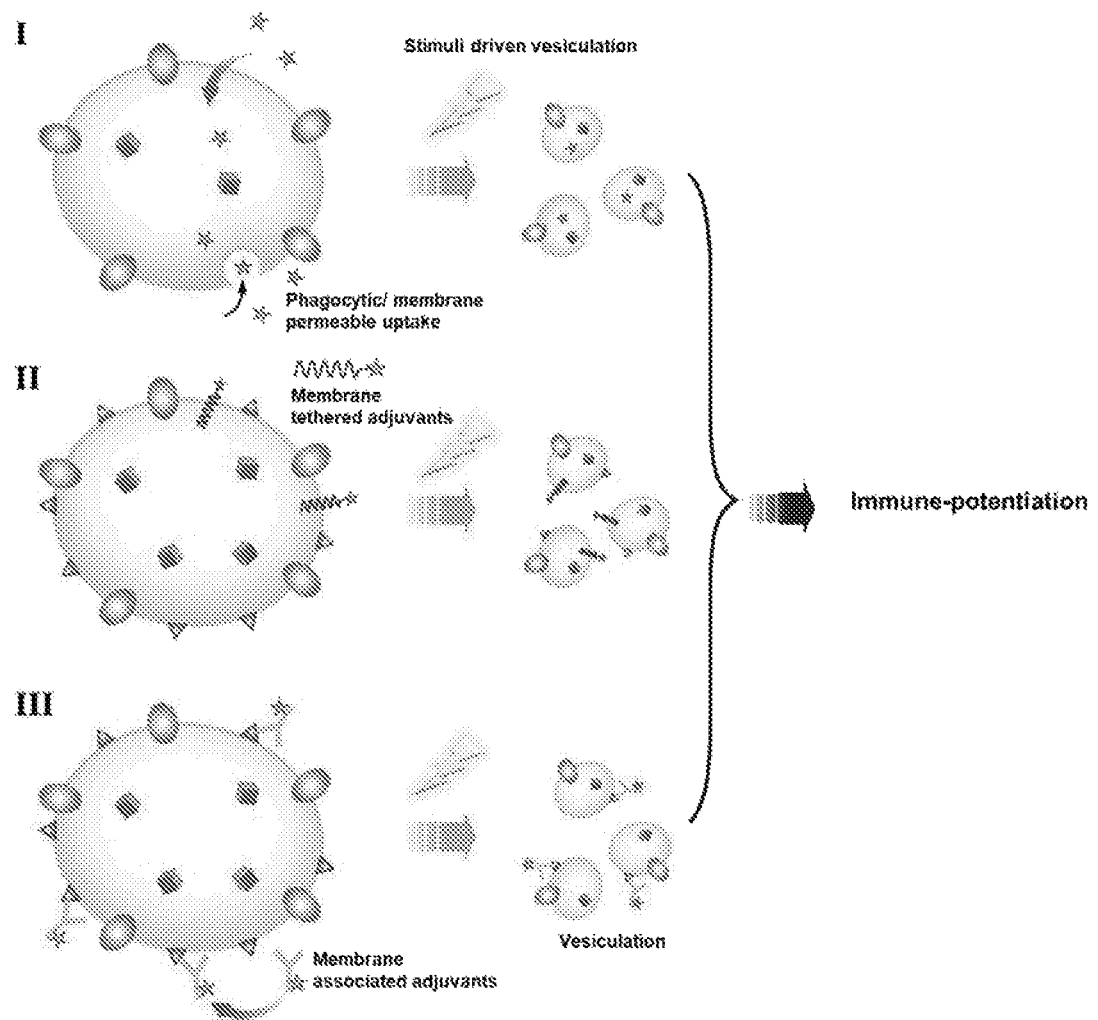
FIG. 1 illustrates pathogenic cell-associating immunologic adjuvants and their function in enhancing subsequent treatments. Immunologic adjuvants are functionalized to associate with pathogenic cells through various means such as intracellular delivery, membrane tethering, and surface binding. The resulting cells are then subjected to treatments that induce generation of adjuvant-associated cellular debris, which can promote adaptive immunity via coordinated antigen and adjuvant transport.

The foregoing and other aspects of the present disclosure will now be described in more detail with respect to other embodiments described herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

As used herein, the terms "comprises," "comprising," "includes," "including," "has," "having," "contains", "containing," "characterized by" or any other variation thereof, are intended to cover a non-exclusive inclusion, subject to any limitation explicitly indicated. For example, a composition, mixture, process or method that comprises a list of elements is not necessarily limited to only those elements but may include other elements not expressly listed or inherent to such composition, mixture, process, or method.

The transitional phrase "consisting of" excludes any elements, steps, or ingredients not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition, method that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Where applicants have defined an invention or a portion thereof with an open-ended term such as "comprising," it should be readily understood that (unless otherwise stated) the description should be interpreted to also describe such an invention using the terms "consisting essentially of" or "consisting of."

As used herein, the term "about" is used to indicate that a value includes for example, the inherent variation of error for a measuring device, the method being employed to determine the value, or the variation that exists among the study subjects. Typically the term is meant to encompass approximately or less than 1%, 2%, 3%, 4%, 5%, 6%, 7%, 8%, 9%, 10%, 11%, 12%, 13%, 14%, 15%, 16%, 17%, 18%, 19% or 20% variability depending on the situation.

The use of the term "or" in the claims is used to mean "and/or" unless explicitly indicated to refer to alternatives only or the alternatives are mutually exclusive, although the disclosure supports a definition that refers to only alternatives and "and/or."

"treating," or "treatment" is referred to herein as administration of a therapeutic composition to a subject with the purpose to cure, alleviate, relieve, remedy, prevent, or ameliorate a disorder, symptoms of the disorder, a disease state secondary to the disorder, or predisposition toward the disorder.

"Subject" as used herein refers to a mammalian subject diagnosed with or suspected of having or developing diseases such as cardiovascular disease, cancer, autoimmune disease, or infection. Exemplary patients may be humans, apes, dogs, pigs, cattle, cats, horses, goats, sheep, rodents and other mammalians with the diseases that can benefit from the treatment.

"Administering" or "Administration" is referred to herein as providing a treatment kit of the present application to a subject. By way of example and not limitation, administration may be performed via parenteral, subcutaneous, intramuscular, intravenous, intra-articular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, and transdermal. For example, injection may be performed by intravenous (i.v.) injection, sub-cutaneous (s.c.) injection, intradermal (i.d.) injection, intraperitoneal (i.p.) injection, or intramuscular (i.m.) injection. One or more such routes may be employed. Parenteral administration can be, for example, by bolus injection or by gradual perfusion over time. Alternatively, or concurrently, administration may be by the oral route.

As used herein, an "immunologic adjuvant formulation" means a formulation that when administered to a subject is capable of inducing an immune response in the subject. When administered in combination with an antigen, the "immunologic adjuvant formulation" are capable of eliciting an antigen-specific immune response. The "immunologic adjuvant formulation" will be associated with cells via cellular internationalization, membrane association, and/or surface ligand binding after being administered by a subject.

As used herein, "cellular internationalization" means an adjuvant formulation that allows intracellular delivery of the desired adjuvants. For instance, "cellular internationalization" of the desired adjuvants may be achieved at least by nanoparticles, exosomes, engineered cell penetrating peptides etc.

As used herein, "membrane association" means an adjuvant formulation that can be partitioned into the cell membrane. For instance, "membrane association" of the desired adjuvants may be achieved at least by lipophilic linkers, amphiphilic adjuvants etc.

As used herein, "surface ligand binding" means an adjuvant formulation that has binding affinity to cell surface moieties and capable of physically associating with cell membrane moieties. For instance, "surface ligand binding" of the desired adjuvants may be achieved at least by antibody, aptamers, sugar formulations etc.

As used herein, a "means for inducing antigen release from a cell" means using a chemical or physical approaches to induce the treated cells to release cellular debris, vesicles, and/or antigens that trigger immune response. For example, the means may comprise chemical agents, biological agents, irradiation, photolytic agents, mechanical disruptions, or a combination thereof.

Unless otherwise defined, all technical and scientific terms used herein have the same meaning as commonly understood by one of ordinary skill in the art to which this invention belongs. All publications, patent applications, patents and other references cited herein are incorporated by reference in their entireties for the teachings relevant to the sentence and/or paragraph in which the reference is presented.

In an embodiment, a treatment kit for enhancing an immunogenicity of released antigens from cells is disclosed. The treatment kit comprises an immunologic adjuvant formulation capable of physically associating with cells; and a means for inducing antigen release from a cell.

In a preferred embodiment, the immunologic adjuvant formulation is a polymeric nanoparticle encapsulating an adjuvant, which comprises: a polymeric shell impermeable to water, and one or more aqueous cores enclosed by the polymeric shell.

The polymeric shell may have a thickness less than 25 nm and the polymeric nanoparticle has an outer diameter of 30-600 nm. Preferably, the thickness is less than 24 nm, 23 nm, 22 nm, 21 nm, 20 nm, 18 nm, 16 nm, 14 nm, 12 nm, or 10 nm. The outer diameter is preferably in a range from 30-550 nm, 30-500 nm, 30-450 nm, 30-400 nm, 30-350 nm, 30-300 nm, 30-250 nm, 30-200 nm, 30-150 nm, 30-100 nm, 35-550 nm, 35-500 nm, 35-450 nm, 35-400 nm, 35-350 nm, 35-300 nm, 35-250 nm, 35-200 nm, 35-150 nm, 35-100 nm, 40-550 nm, 40-500 nm, 40-450 nm, 40-400 nm, 40-350 nm, 40-300 nm, 40-250 nm, 40-200 nm, 40-150 nm, 40-100 nm, 45-550 nm, 45-500 nm, 45-450 nm, 45-400 nm, 45-350 nm, 45-300 nm, 45-250 nm, 45-200 nm, 45-150 nm, 45-100 nm, 50-550 nm, 50-500 nm, 50-450 nm, 50-400 nm, 50-350 nm, 50-300 nm, 50-250 nm, 50-200 nm, 50-150 nm, or 50-100 nm.

In one embodiment, the polymeric shell is formed of an amphiphilic polymer that contains a non-polar segment and a polar terminal group. Examples of the non-polar segment include, but are not limited to, poly(lactic acid), poly(lactic-co-glycolic acid) (PLGA), polycaprolactone, and polyurethane. The lactic acid to glycolic acid molar ratio of the PLGA varies from 1:99 to 99:1, from 10:90 to 90:10, from 15:85 to 85:15, from 20:80 to 80:20, from 25:75 to 75:25, from 30:70 to 70:30. Preferably, the lactic acid to glycolic acid molar ratio of the PLGA is 50:50 or 75:25. The polar terminal group can be a negatively charged group, a positively charged group, a zwitterionic group, or a neutral group. Examples of the negatively charged group include a carboxylic acid, a succinic acid, and a sulfonic acid. Examples of the positively charged group include an amine and an amidine. Examples of the zwitterionic group include a carboxybetaine and a sulfobetaine. An example of the neutral group is a saccharide.

An exemplary polymeric shell is formed of a polymer containing poly(lactic-co-glycolic acid) as the non-polar segment and a carboxylic acid as the polar terminal group.

The polymeric nanoparticle described herein can be a polymeric hollow nanoparticle platform with a defect-free polymeric shell having a thickness of 25 nm or less. The hollow polymeric nanoparticle typically has an outer diameter between 30 and 600 nm.

By minimizing the shell thickness, the polymeric nanoparticle can be formed with a large interior aqueous space capable of maximizing the cargo loading. For particles above 100 nm in outer diameter, the interior aqueous space can possess a diameter at least 80% of the particle's outer diameter or can be of multiple compartments with a large collective volume. High efficiency encapsulation of hydrophilic dyes and nucleic acids are demonstrated with the thin-shell hollow nanoparticles in the absence of complementary binding molecules. The thin-shell nanoparticles are demonstrated to be resistant to osmotic stress, a feature attributable to complete, defect-free polymeric shell that is impermeable to water. The polymeric nanoparticle of this application can be used for delivering bioactive agents in various fields, including drug delivery and vaccine development.

Polymeric nanoparticles, particularly those consisting of biodegradable and biocompatible polymers such as poly(lactic-co-glycolic acid)(PLGA), have received considerable attention in nanomedicine research because of the polymer's numerous features including biocompatibility, biodegradability, and synthetic flexibility. However, due to the polymer's inherent hydrophobicity, PLGA-based nanoparticles have been limited to the delivery of water-insoluble compounds in clinical. Encapsulation of hydrophilic and macromolecular cargoes in polymeric nanoparticles remains a challenge as polymers tend to form solid nanospheres with little or no aqueous core space to carry hydrophilic and macromolecular cargoes, e.g., siRNA.

Given that macromolecular encapsulation is common in natural nanoparticulates in the form of viruses, an ideal nanocarrier should possess a thin shell enclosing a large aqueous volume for the packaging of bioactive molecules. The thin shell is also preferably defect free and water impermeable to allow reliable cargo encapsulation.

In an embodiment, a method of treating a disease is provided. The method comprises administering to a subject in need thereof an immunologic adjuvant formulation capable of physically associating with cells; and administering to the subject in need thereof a means for inducing antigen release from a cell. Examples of the disease includes, but is not limited to, cardiovascular disease, cancer, autoimmune disease, or infection.

Further disclosed in detail herein is a method of preparing the above-described polymeric nanoparticle.

In general, the thin-shell hollow nanoparticle is prepared based on a double emulsion process using amphiphilic polymers with high contrast of polarity at their terminus. More specifically, a solution of carboxyl-terminated PLGA in dichloromethane (DCM) is first used to emulsify an aqueous phase containing a cargo under sonic dispersion to form an emulsion. The emulsion thus formed is subsequently emulsified in an outer aqueous phase using fluidic dispersion.

By adjusting the polymer concentration and dispersion force or using polymers with defined length and sharp polarity in the double emulsion process, the preparation method described above can provide hollow polymeric nanoparticles with outer diameters between 30 and 600 nm, e.g., 30-40 nm and 100-600 nm.

The nanoparticles are prepared based on a water-oil-water double emulsion process in which polymers dissolved in a solvent system is first used to emulsify an aqueous phase. The emulsion is subsequently emulsified by a secondary aqueous phase. The inner and outer aqueous phases can be of any polar solution, e.g., water, acetic acid, and ethanol. The aqueous phase contains solubilized molecules to modulate the solution's acidity and viscosity, which include sodium phosphate and sodium bicarbonate. In one embodiment, water is used as an anti-solvent for the nanoparticle preparation.

The water-oil-water double emulsion method described above for preparing the polymeric nanoparticle of in the present application has two key features; namely, (i) emulsion between different phases is achieved through polymers with inherently high contrast in polarity (PLGA with a carboxyl-terminal group) rather than using an surfactant, e.g., vitamin E-D-α-tocopherol polyethylene glycol succinate and poly(vinyl alcohol), which enhances the emulsifying capability to minimize polymer shell thickness and has a higher commercial value without using surfactant materials; and (ii) controlled fluidic dispersion using either a microfluidizer or sonication for the second emulsion process to balance homogenization of the oil phase and retention of encapsulated cargo in the inner aqueous phase.

The polymeric nanoparticle prepared by the above-described method serves as a platform technology for drug delivery, theranostics, and vaccine development applications. It can facilitate delivery of a large class of bioactive agents, including small molecules, peptides, nucleic acids, and proteins, to enhance their therapeutic potency. The thin-shell polymeric hollow nanoparticles can be used to encapsulate bioactive agents, including but not limited to small molecules, peptides, proteins, nucleic acids, imaging agents, inorganic nanoparticles, organic nanoparticles, and any combination of the above. The surface of the platform can be optionally decorated with functional moieties, including small molecules, peptides, proteins, nucleic acids, imaging agents, nanoparticles, for different applications such as long-circulating drug delivery, targeted drug delivery, and antigen delivery.

Without further elaboration, it is believed that one skilled in the art can, based on the above description, utilize the present invention to its fullest extent. The following specific examples are, therefore, to be construed as merely illustrative, and not limitative of the remainder of the disclosure in any way whatsoever. All publications cited herein are incorporated by reference.

EXAMPLES

Preparation of Polymeric Nanoparticles

Thin-shell polymeric nanoparticles were produced according to a protocol including the following steps:
1. preparing 10 mg/mL carboxy-terminated PLGA polymers in DCM.
2. emulsifying 50 μL of inner aqueous phase in 500 μL of PLGA/DCM solution to form a first emulsion. Probe sonicate continuously at 50% sonication amplitude for 30 seconds.
3. emulsifying the first emulsion in 5 mL of aqueous solution and disperse the mixture under controlled fluidic shear using a microfluidizer to form a second emulsion.
4. adding an additional 30 mL of aqueous solution to the second emulsion and evaporate the solvent at 35° C.
5. evaporating the DCM in a fume hood for 3 hours to afford a solution.
6. isolating particles from the solution by an ultracentrifuge at 22 kG for 35 min.
7. re-dispersing the particles in a desired solution.

Characterization and Encapsulation of Polymeric Nanoparticles

By employing the steps described above, hollow polymeric nanoparticles with an average diameter of 110.9 nm were prepared. Statistical average of the particles' shell thickness was derived based on parameters obtained by nanoparticle tracking analysis. Based on the total polymer weight, PLGA density, and the number of resulting nanoparticles, it was calculated that the nanoparticles have a statistical average of 16.5 nm in shell thickness. Unexpectedly, certain polymeric nanoparticles had diameters less than 40 nm.

The thin-shell hollow nanoparticles were found to be osmotically resistant resulting from the water impermeable polymeric shells. In a test, 100 nm hollow nanoparticles encapsulating a hydrophilic red food coloring were suspended in solutions ranging from water to 3×PBS, the difference in osmolarity (between 0 to 850 Osmo/kg) did not cause the hollow nanoparticles to release their cargoes. Following 10 min of incubation in their respective solutions, nanoparticles were pelleted under centrifugation at 30,000 g for 5 min, and the resulting pellets showed similar, reddish color indicating retention of hydrophilic dye in the particles. Detection of the supernatant for the released dye based on an absorbance method showed no detectable signals. The study shows that despite having a thin polymeric shell below 20 nm, the hollow nanoparticles had defect-free shells that made them resistant to osmotic stress.

To further demonstrate that the shell of the thin-shell hollow nanoparticles were solid rather than fluid, hollow nanoparticles were subjected to mechanical stress to break the shell. In a cryo-EM visualization, a broken hollow nanoparticle was observed. The observed image of the broken hollow nanoparticles was indicative of a hollow sphere with a solid shell, in contrast to the polymeric vesicles that undergo vesicular reorganization upon mechanical perturbation. The solid polymeric shell led to the water impermeability and osmotic resistance that were not observed in known hollow nanostructures.

A distinguishing feature of the thin-shell polymeric nanoparticle platform is its capacity to encapsulate a large amount of hydrophilic cargoes with its large interior aqueous space. The thin-shell hollow nanoparticles were subjected to encapsulate several bioactive agents, including siRNA and an immunological adjuvant cyclic di-GMP. Unexpectedly, high encapsulation efficiency was achieved for hydrophilic contents of various length scales, including small molecules (e.g., sulfo-cy5, cyclic di-GMP, and cyclic cGAMP), peptides (e.g., ovalbumin peptide OTI (SIINFEKL) or OTII (AAHAEINEA)), nucleic acids (e.g., CpG-oligodeoxynucleotides, 20-mer single stranded DNA, and 20-mer siRNA), and proteins (e.g., bovine serum albumin (BSA) and CRISPR-Cas9 nuclease), which were successfully encapsulated with an efficiency above 30% within the compounds' solubility limits. For example, siRNA was encapsulated at an efficiency of 50% with a final loading yield of about 1 nmol per mg of nanoparticles and cyclic di-GMP was encapsulated at a 37% loading efficiency. Silencing of a green fluorescent protein (GFP) gene in GFP-expressing HeLa cells was observed using siRNA loaded thin-shell hollow nanoparticles.

Encapsulation of Polymeric Nanoparticles with Hydrophilic Macromolecules

An assay was performed to evaluate the encapsulation efficiency of polymeric nanoparticles for two hydrophilic macromolecules, i.e., a nucleic acid (dye-labelled 20-mer single stranded DNA) and a protein (dye-labelled BSA).

Figure 2:
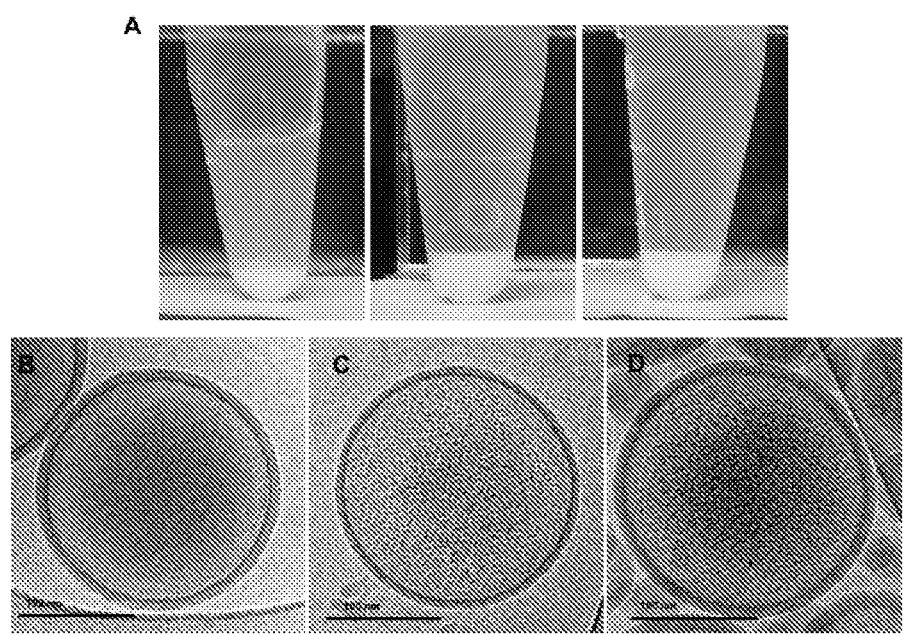
FIG. 2 depicts encapsulation efficiency of polymeric nanoparticles for a nucleic acid and a protein. A: Observation of empty nanoparticles (left), nanoparticles loaded with dye-labelled DNA (middle), and nanoparticles loaded with dye-labelled bovine serum albumin (right) following pelleting by ultracentrifugation. Distinctive colored pellets indicate successful encapsulation of DNA and BSA proteins. B: Empty nanoparticles visualized by cryoEM. C: DNA-loaded nanoparticles visualized by cryoEM. D: BSA protein-loaded nanoparticles visualized by cryoEM. Effective DNA and protein loading could be observed through the highly grainy textures inside nanoparticles.

Please refer to FIG. 2 for a depiction of encapsulation efficiency of polymeric nanoparticles for a nucleic acid and a protein. In this example, effective encapsulation of a nucleic acid and a protein was demonstrated using dye-labelled 20-mer single stranded DNA (A; middle) and dye-labelled BSA (A; right). Upon pelleting the nanoparticles, the particle pellets were found to be yellow colored (indicative of the yellowish FAM dye label) as opposed to the white pellet of the empty nanoparticles (A; left). Fluorescence quantification indicates that the nanoparticles unexpectedly exhibited encapsulation efficiencies of 42% and 35% for the nucleic acid and protein, respectively.

Effective encapsulation of the nucleic acid and protein was also visualized using cryoEM. While empty particles showed a plain, even texture in its aqueous core (FIG. 2B), DNA-loaded particles (FIG. 2C) and BSA-loaded particles (FIG. 2D) showed highly grainy textures that are characteristics of concentrated biological contents under cryoEM. Based on the loading concentration of 8 mM DNA and 50 mg/mL BSA for the present embodiments, the DNA-loaded nanoparticle contained about 3500 DNA molecules and the BSA-loaded nanoparticle contains about 260 proteins. Importantly, such high loading of a nucleic acid and a protein have not been previously achieved. Indeed, known PLGA-based nanoformulations consistently showed very poor nucleic acids encapsulation, and polycationic polymers had to be employed to neutralize the negative charges on nucleic acids to enhance loading. For example, see Shi et al., Angew Chem Int Ed Engl, 2011, 50(31): 7027-31; and Woodrow et al., Nature Materials, 2009, 8(6): 526-533.

These results described above indicate that the thin-shell polymeric nanoparticles of the present application unexpectedly exhibited high encapsulation efficiency, i.e., high loading efficiency, for hydrophilic macromolecules in their native, soluble state, highlighting the advantage and uniqueness of the thin-shell hollow nanoparticles.

Effect of Polymeric Nanoparticles on Encapsulation and Controlled Release of Stimulator of Interferon Gene (STING) Agonists for Immune Stimulation in Lymph Nodes An assay was performed to evaluate the effect of polymeric nanoparticles on encapsulation and controlled release of STING agonists for immune stimulation in lymph nodes.

FIG. 3 depicts the effect of polymeric nanoparticles on encapsulation and controlled release of STING agonists for immune stimulation. In this example, the present platform was applied for vaccine development. A major technical challenge in preparing nanoparticle vaccines lies in reliably associating antigens and adjuvants on a nanoscale substrate. For example, see Brannon-Peppas et al., Adv Drug Deliv Rev, 2004, 56(11): 1649-59; and Lima-Tenorio et al., Int J Pharm, 2015, 493(1-2): 313-27. To overcome this technical challenge, thin-shell polymeric hollow nanoparticles were used to package a high density of functional cargoes using a biodegradable polymer, i.e., PLGA.

Figure 3A:
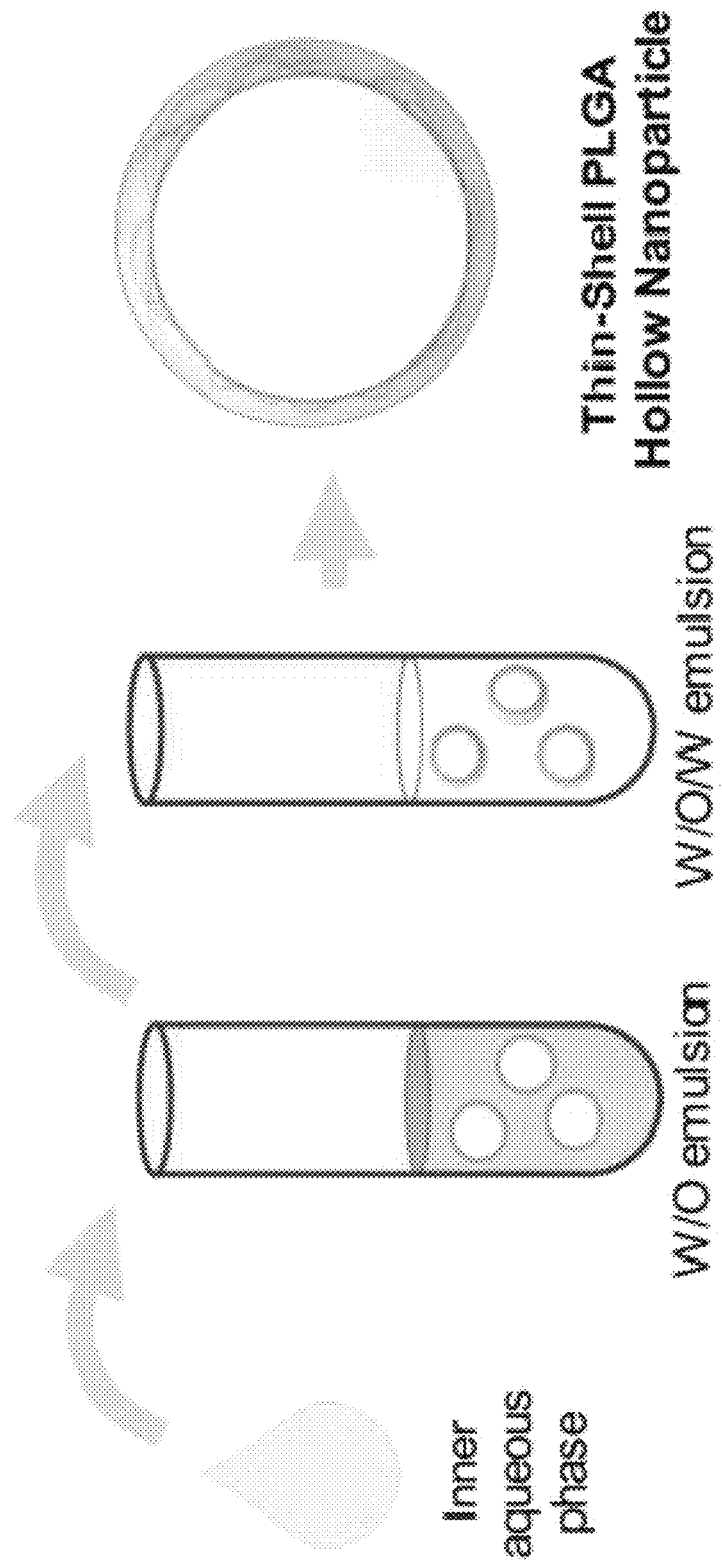
FIG. 3 depicts the effect of polymeric nanoparticles on encapsulation and controlled release of STING agonists for immune stimulation. A: Preparation of adjuvant-loaded thin-shell hollow nanoparticles. B: Size of nanoparticles as measured by nanoparticle tracking analysis. C: Encapsulation of cyclic-di-GMP as verified by gradient HPLC. D: CryoEM visualization of thin-shell hollow nanoparticles. E: Cargo release study revealed a pH-sensitive triggered release profile for the nanoparticles.
Figure 3B:
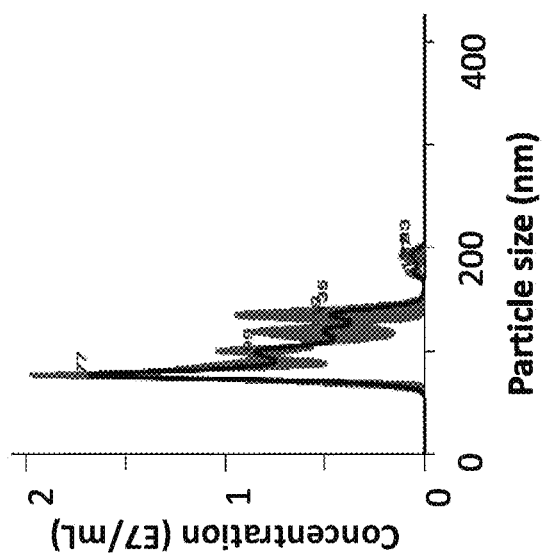
Figure 3C:
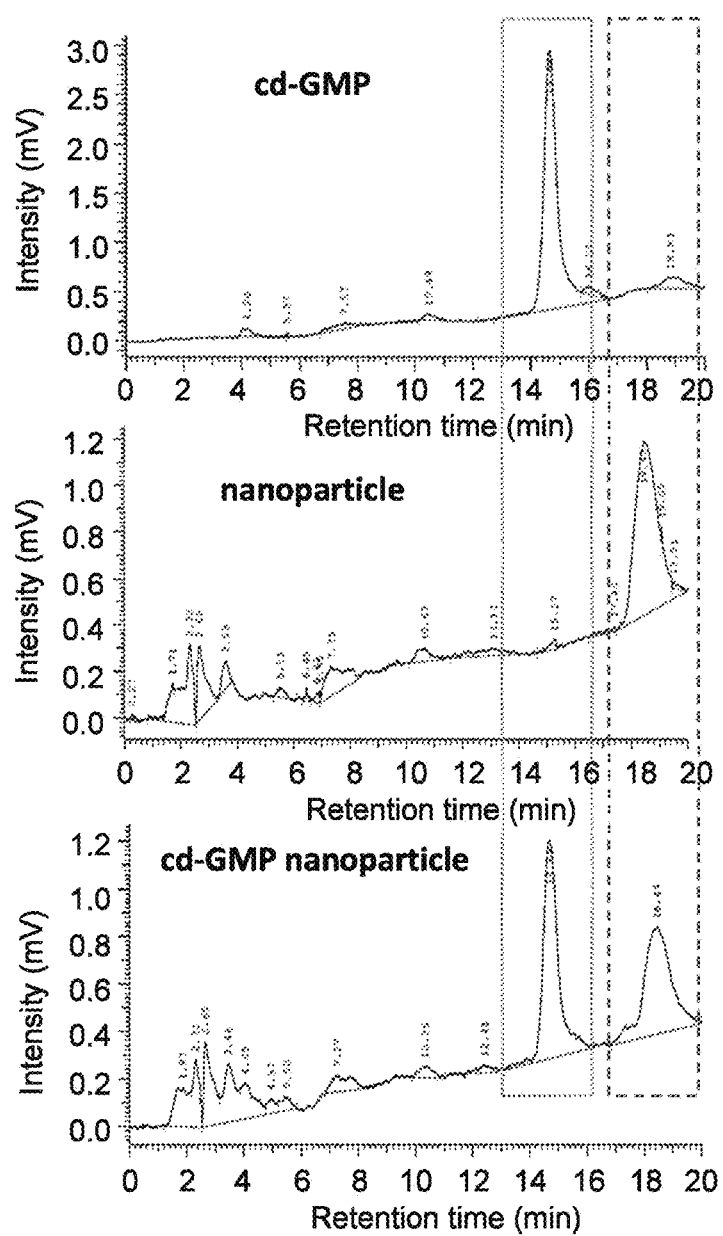
Figure 3D:
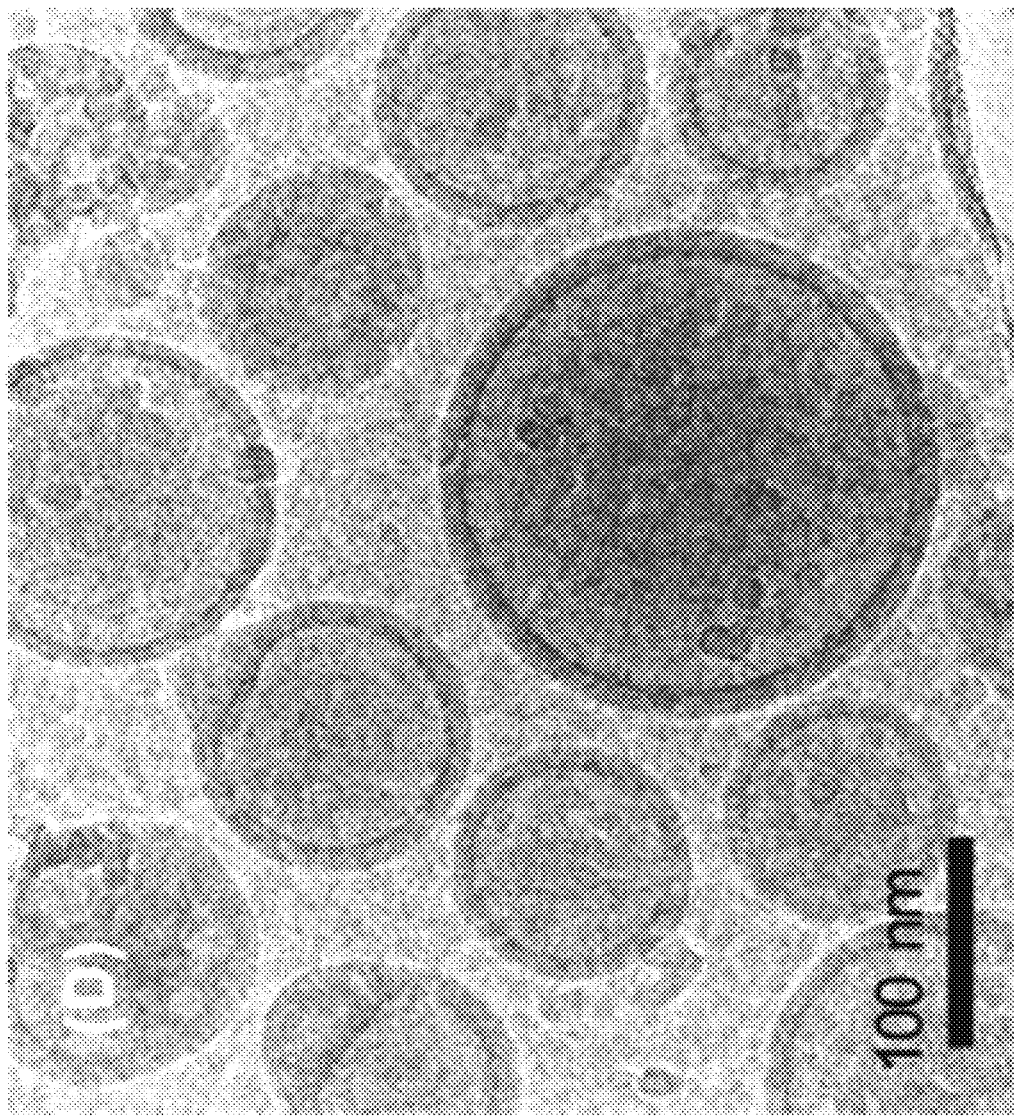
Figure 3E:
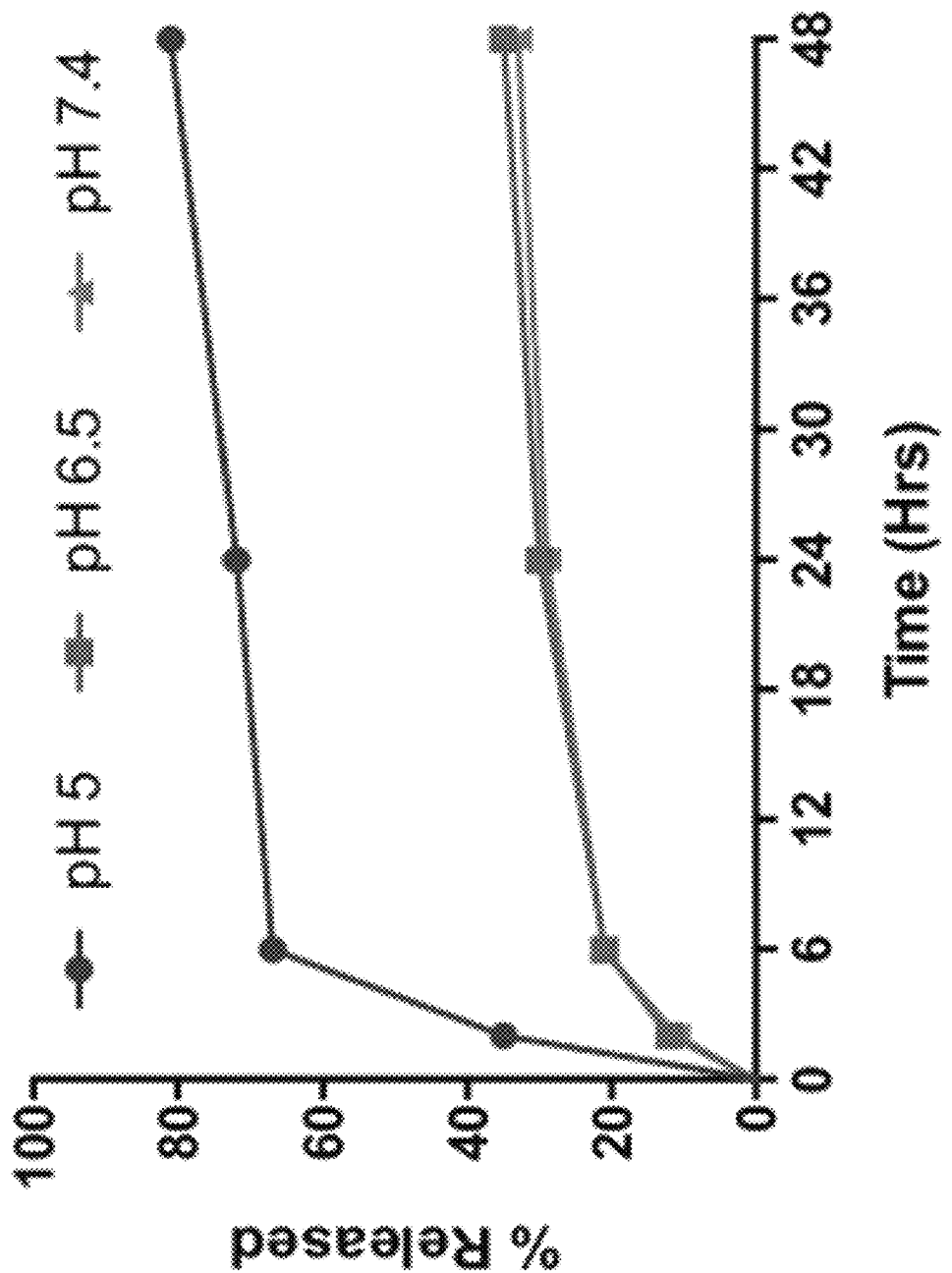

More specifically, hollow particles between 100 to 200 nm in diameter were prepared using a double emulsion process (FIGS. 3A and 3B). They efficiently encapsulated a STING agonist adjuvant, cyclic di-GMP (cd-GMP), at about 40% efficiency (FIG. 3C), which is notable as nucleic acids and hydrophilic cargoes are notoriously difficult to encapsulate in nanoparticle platforms. The high encapsulation efficiency yielded approximately 2,000 STING agonist molecules per nanoparticle. No nanoformulations of STING agonists based on polymeric nanoparticles have been reported. Examination by cryoEM revealed large interior cores in these hollow nanoparticles, which were responsible for the high loading efficiency of cd-GMP (FIG. 3D). Upon intracellular delivery, the thin polymeric shell of the hollow nanoparticles was triggered by acidic pH to rapidly release the interior content (FIG. 3E).

These results indicate that the thin-shell polymeric nanoparticles enabled effective preparation of synthetic vaccines.

Evaluation of STING Agonist-Loaded Nanoparticles on Enhancing Lymphatic Cytokines while Minimizing Systemic Cytokines An assay was performed to evaluate STING agonist-loaded nanoparticles on enhancing lymphatic cytokines while minimizing systemic cytokines.

FIG. 4 depicts STING agonist-loaded nanoparticles on enhancing lymphatic cytokines while minimizing systemic cytokines. Immune activation by the cd-GMP-loaded nanoparticles was first examined in vitro using a mouse dendritic cell line, JAWSII. Following 24 hours of incubation with either free cd-GMP or cd-GMP nanoparticles, the culture supernatants were collected for ELISA analysis to quantify the levels of TNF-α, IL-6, and IFN-s. As compared to free cd-GMP formulation, the nanoparticle formulation more effectively triggered the production of TNF-α, IL-6, and IFN-β(FIGS. 4A, 4B, and 4C). CD80 expression on the cells was also enhanced when incubated with the nanoparticle formulation as compared to an equivalent dose of free cd-GMP (FIG. 4D). It was observed that the nanoparticles enhanced the adjuvanticity of the STING agonist by about 30 folds, attributable to increased intracellular delivery by the nanocarrier. It can be inferred that the free cyclic-dinucleotide is not readily membrane permeable and may not easily access its cytosolic target. Upon nanoparticle encapsulation, cellular uptake is enhanced via particle endocytosis and the subsequent intracellular release facilitates cytosolic entry of cd-GMP, thereby enhancing its immune potentiating effect.

Figure 4A:
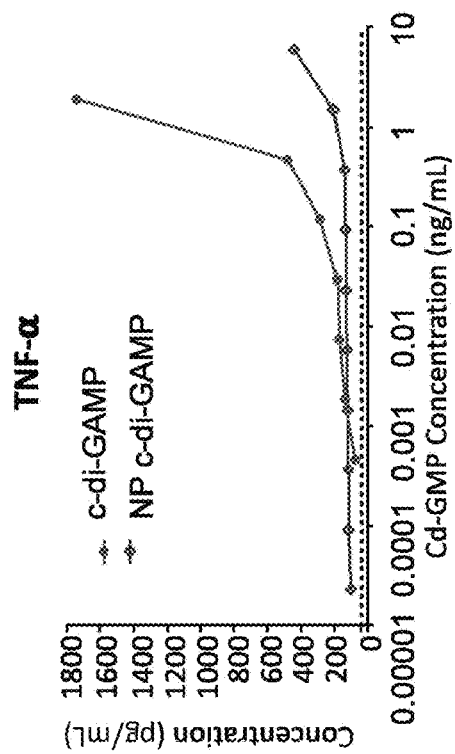
FIG. 4 depicts STING agonist-loaded nanoparticles on enhancing lymphatic cytokines while minimizing systemic cytokines. A: Induction of TNF-α in a mouse dendritic cell line following incubation with cd-GMP nanoparticles and free cd-GMP. B: Induction of IL-6 in the same mouse dendritic cell line. C: Induction of IFN-β in the mouse dendritic cell line. D: Activation of JAWSII upon incubation with equivalent doses of cd-GMP in free molecule form and in nanoparticle formulation. E: Quantification of lymph node IFN-s 48 hours following footpad injection of free cd-GMP or nanoparticle cd-GMP. F: Level of systemic TNF-α following footpad injection of free cd-GMP and nanoparticle cd-GMP.
Figure 4B:
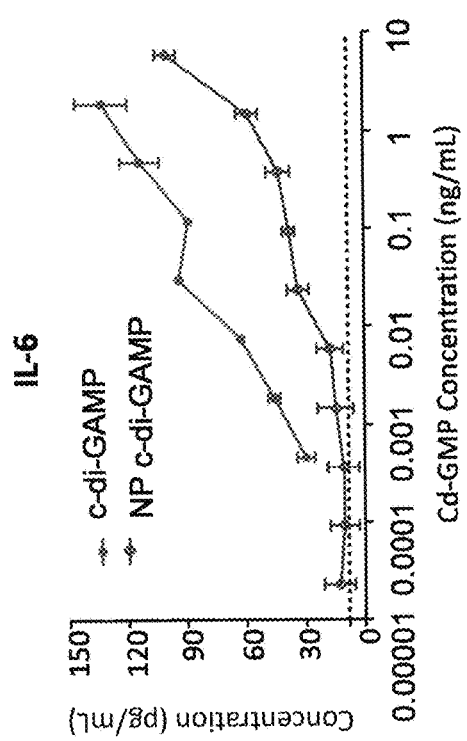
Figure 4C:
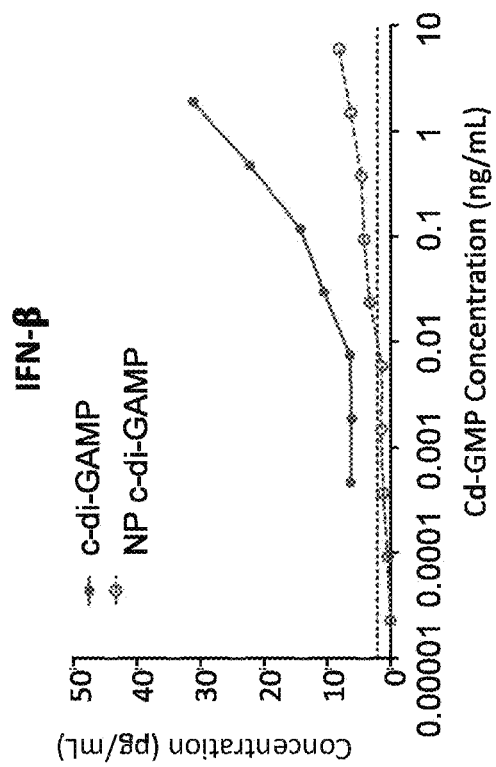
Figure 4D:
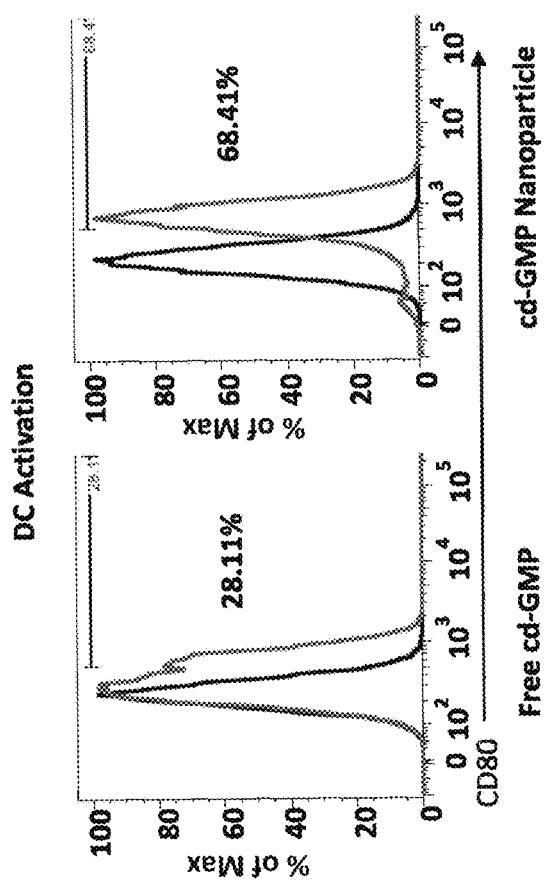
Figure 4E:
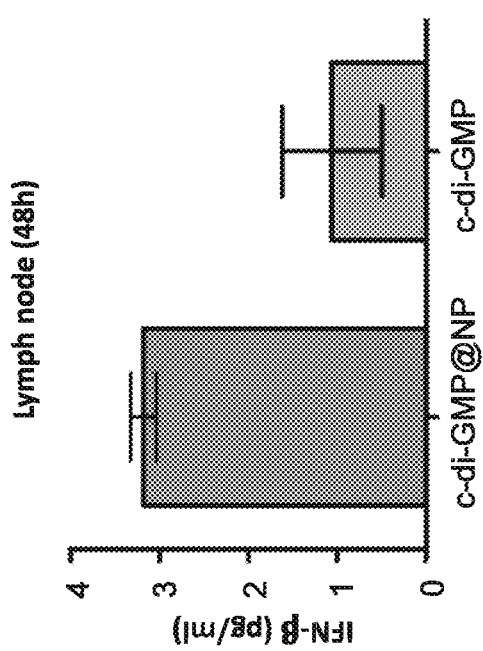
Figure 4F:
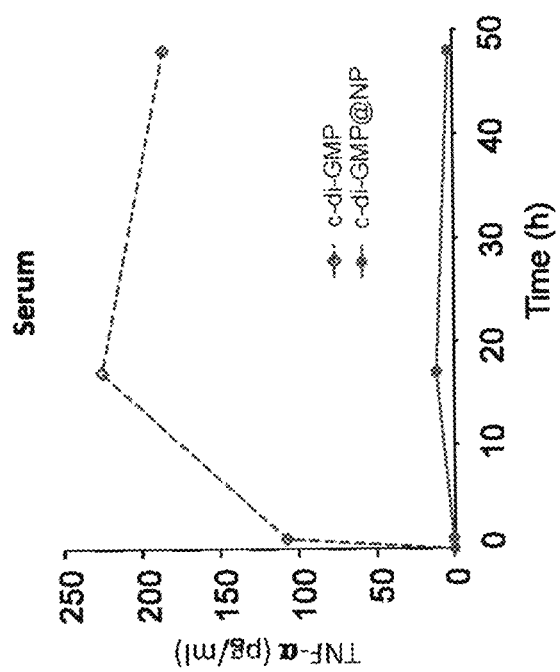

Immune potentiation by the cd-GMP nanoparticles was further compared to free cd-GMP in vivo in mice. 48 hours following footpad injections, the draining popliteal lymph nodes were collected for IFN-β quantification. It was observed that the nanoparticle formulation induced a significantly higher level of IFN-β in the lymph node (FIG. 4E), which is important for proper T cell maturation. In addition, the systemic level of TNF-α, an indicator of reactogenicity, was also monitored following the footpad administration of free cd-GMP and cd-GMP nanoparticles. It was observed that the nanoparticles resulted in a significantly lower serum level of TNF-α, which reflects the nanoparticles' distribution in the lymphatic system. The free cd-GMP, on the other hand, induced an elevated level of serum TNF-α and these small molecules could freely diffuse into the blood stream (FIG. 4F).

These results indicate that STING agonist-loaded nanoparticles effectively enhanced lymphatic cytokines for lymph node-targeted immune potentiation.

Treatment Modality Based on a Cell-Associating Immunologic Adjuvant

In one embodiment, the treatment kit and the method described herein can be used to treat diseases, for example, cardiovascular disease, cancer, autoimmune disease, or infection. In one embodiment, the treatment kit and the method described herein can be used to cancers, such as cancer of the oral cavity and pharynx (lip, tongue, salivary gland, floor of mouth, gum and other mouth, nasopharynx, tonsil, oropharynx, hypopharynx, other oral/pharynx); cancers of the digestive system (esophagus; stomach; small intestine; colon and rectum; anus, anal canal, and anorectum; liver; intrahepatic bile duct; gallbladder; other biliary; pancreas; retroperitoneum; peritoneum, omentum, and mesentery; other digestive); cancers of the respiratory system (nasal cavity, middle ear, and sinuses; larynx; lung and bronchus; pleura; trachea, mediastinum, and other respiratory); cancers of the mesothelioma; bones and joints; and soft tissue, including heart; skin cancers, including melanomas and other non-epithelial skin cancers; Kaposi's sarcoma and breast cancer; cancer of the female genital system (cervix uteri; corpus uteri; uterus, ovary; vagina; vulva; and other female genital); cancers of the male genital system (prostate gland; testis; penis; and other male genital), cancers of the urinary system (urinary bladder; kidney and renal pelvis; ureter; and other urinary); cancers of the eye and orbit; cancers of the brain and nervous system (brain; and other nervous system); cancers of the endocrine system (thyroid gland and other endocrine, including thymus); lymphomas (Hodgkin's disease and non-Hodgkin's lymphoma), multiple myeloma, and leukemias (lymphocytic leukemia; myeloid leukemia; monocytic leukemia; and other leukemias).

In an embodiment, the immunologic adjuvant formulation comprises a polymeric nanoparticle encapsulating an adjuvant, and the polymeric nanoparticle may further comprise: a polymeric shell impermeable to water, and one or more aqueous cores enclosed by the polymeric shell. In a preferred embodiment, the adjuvant comprises MPLA, CpG, poly(I:C), variants of cyclic-dinucleotides, an agonist to a cytoplasmic pattern recognition receptor such as cyclic di-GMP or cyclic GAMP, or a stimulator of interferon genes (STING).

Figure 5:
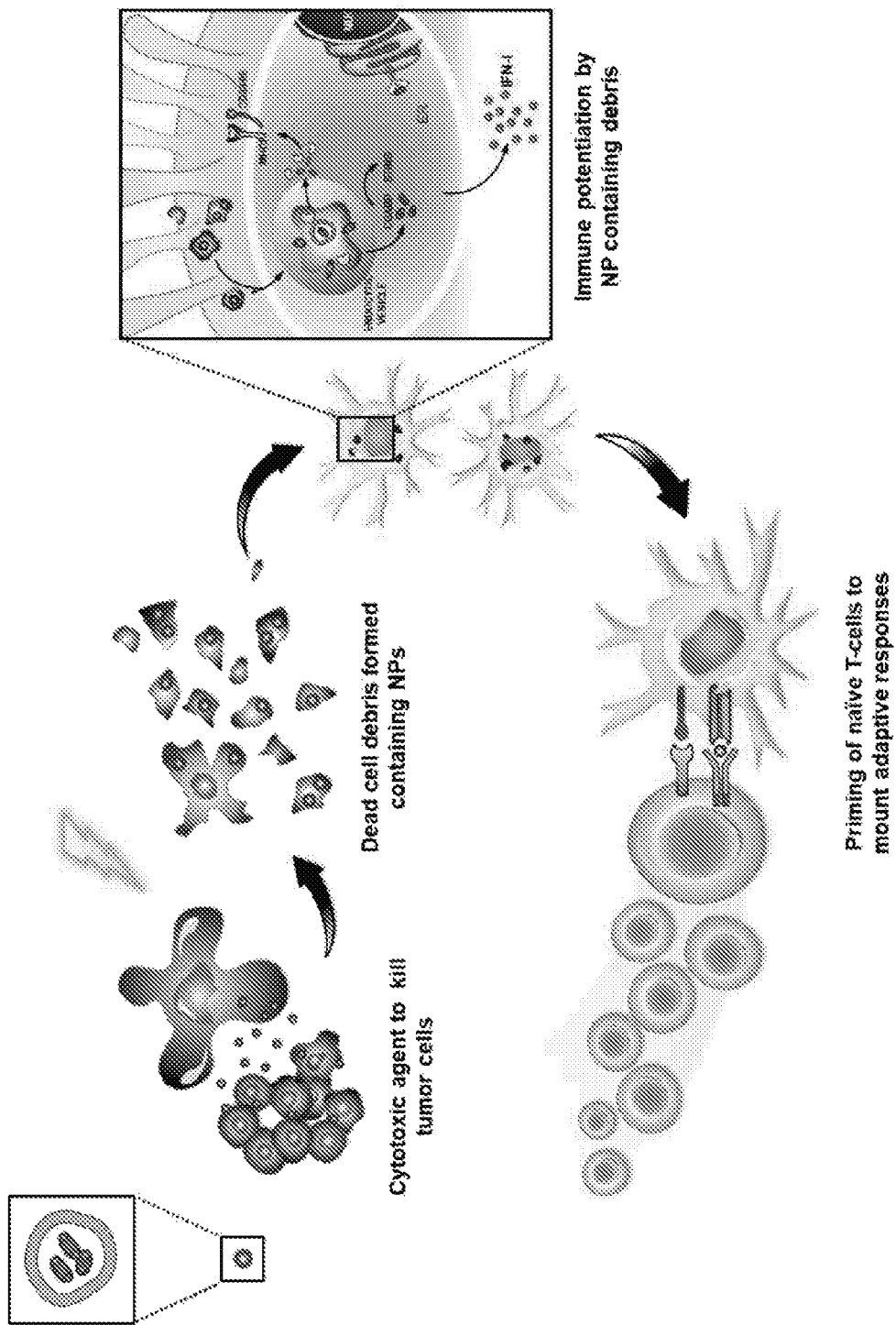
FIG. 5 depicts a treatment modality based on a tumor cell-associating immunologic adjuvant (cGAMP-loaded nanoparticle). Following nanoparticle uptake, the cells containing exogenous adjuvants are then treated to generate a dead cellular debris. The cellular debris containing the exogenous adjuvants subsequently triggers adaptive immunity to improve treatment outcome.

Please refer to FIG. 5 for depiction of a treatment modality based on a tumor cell-associating immunologic adjuvant (cGAMP-loaded nanoparticle). In one embodiment of the present application, 2'3'-cGAMP is encapsulated inside a polymeric hollow nanoparticle to enhance cell internalization via endocytosis. cGAMP is an agonist to cytoplasmic pattern recognition receptor, a stimulator of interferon genes (STING) that activate the TBK1/interferon regulatory factor 3 (IRF3)/type 1 interferon (IFN) signaling. By facilitating cGAMP association with cells, the adjuvant formulation primes the antigens for immune processing. Upon treatment that induces cell death by a means of for inducing antigen release, cellular debris are then processed along with the exogenously delivered adjuvants from the adjuvant formulation, enabling enhanced adaptive immunity for cell killing (FIG. 5).

In an embodiment, the means for inducing antigen release may comprise chemical agents, biological agents, irradiation, photolytic agents, mechanical disruptions, or a combination thereof.

In a preferred embodiment, the chemical agents comprise any cytotoxic agents known in the art. For example, the cytotoxic agent comprises Monomethyl auristatin E (MMAE), Monomethyl auristatin F (MMAF), mertansine (DM1), anthracycline, pyrrolobenzodiazepine, α-amanitin, tubulysin, benzodiazepine, erlotinib, bortezomib, fulvestrant, sunitinib, letrozole, imatinib mesylate, PTK787/ZK 222584, oxaliplatin, leucovorin, rapamycin, lapatinib, lonafarnib (SARASAR®, SCH 66336), sorafenib, gefitinib, AG1478, AG1571, alkylating agent; alkyl sulfonate; aziridines; ethylenimine; methylamelamine; acetogenins; camptothecin; bryostatin; callystatin; CC-1065; cryptophycins; dolastatin; duocarmycin; eleutherobin; pancratistatin; sarcodictyin; spongistatin; chlorambucil; chlornaphazine; cholophosphamide; estramustine; ifosfamide; mechlorethamine; mechlorethamine oxide hydrochloride; melphalan; novembichin; phenesterine; prednimustine; trofosfamide; uracil mustard; carmustine; chlorozotocin; fotemustine; lomustine; nimustine; ranimustine; calicheamicin; dynemicin; clodronate; esperamicin; neocarzinostatin chromophore; aclacinomysins; actinomycin; authramycin; azaserine; bleomycins; cactinomycin; carabicin; caminomycin; carzinophilin; chromomycinis; dactinomycin; daunorubicin; detorubicin; 6-diazo-5-oxo-L-norleucine; doxorubicin; epirubicin; esorubicin; idarubicin; marcellomycin; mitomycin; mycophenolic acid; nogalamycin; olivomycins; peplomycin; potfiromycin; puromycin; quelamycin; rodorubicin; streptonigrin; streptozocin, tubercidin, ubenimex, zinostatin, zorubicin; methotrexate; 5-fluorouracil (5-FU); denopterin; pteropterin; trimetrexate; fludarabine; 6-mercaptopurine; thiamiprine; thioguanine; ancitabine; azacitidine; 6-azauridine; carmofur; cytarabine; dideoxyuridine; doxifluridine; enocitabine; floxuridine; calusterone; dromostanolone propionate; epitiostanol; mepitiostane; testolactone; aminoglutethimide; mitotane; trilostane; frolinic acid; aceglatone; aldophosphamide glycoside; aminolevulinic acid; eniluracil; amsacrine; bestrabucil; bisantrene; edatraxate; defofamine; demecolcine; diaziquone, elformithine; elliptinium acetate; epothilone; etoglucid; gallium nitrate; hydroxyurea; lentinan; lonidainine; maytansine; ansamitocins; mitoguazone; mitoxantrone; mopidanmol; nitraerine; pentostatin; phenamet; pirarubicin; losoxantrone; podophyllinic acid; 2-ethylhydrazide; procarbazine; razoxane; rhizoxin; sizofiran; spirogermanium; tenuazonic acid; triaziquone; 2,2',2"-trichlorotriethylamine; trichothecene; urethan; vindesine; dacarbazine; mannomustine; mitobronitol; mitolactol; pipobroman; gacytosine; arabinoside; cyclophosphamide; thiotepa; taxoid; paclitaxel; doxetaxel; chloranbucil; gemcitabine; 6-thioguanine; mercaptopurine; methotrexate; cisplatin; carboplatin; vinblastine; platinum; etoposide; ifosfamide; mitoxantrone; vincristine; vinorelbine; novantrone; teniposide; edatrexate; daunomycin; aminopterin; xeloda; ibandronate; topoisomerase inhibitor; difluoromethylornithine (DMFO); retinoid; capecitabine; or a combination thereof.

In a preferred embodiment, the photolytic agents, which is generally a photosensitizing agent used in the photodynamic therapy, comprises Photofrin, Laserphyrin, Aminolevulinic acid (ALA), Silicon Phthalocyanine Pc 4, m-tetrahydroxyphenylchlorin (mTHPC), chlorin e6 (Ce6), Allumera, Levulan, Foscan, Metvix, Hexvix, Photochlor, Photosens, Photrex, Lumacan, Visonac, Amphinex, Verteporfin, Purlytin, ATMPn, Zinc phthalocyanine (ZnPc), Protoporphyrin IX (PpIX), Pyropheophorbidea (PPa), Pheophorbide a (PhA), or a combination thereof.

The means for inducing antigen release may be administered to the subject in need before or after administration of the immunologic adjuvant formulation. In this course of treatments, the means for inducing antigen release and the immunologic adjuvant formulation are formulated as two distinct doses for being administered at different times.

Alternatively, the means for inducing antigen release may be administered to the subject in need at the same time as the immunologic adjuvant formulation. In this course of treatments, the means for inducing antigen release from a cell can be formulated with or encapsulated in the immunologic adjuvant formulation as a single dose or two distinct doses for being administered simultaneously. For example, the adjuvants and the cytotoxic agents may be formulated in one nanoparticle or conjugated to one antibody.

Figure 6A:
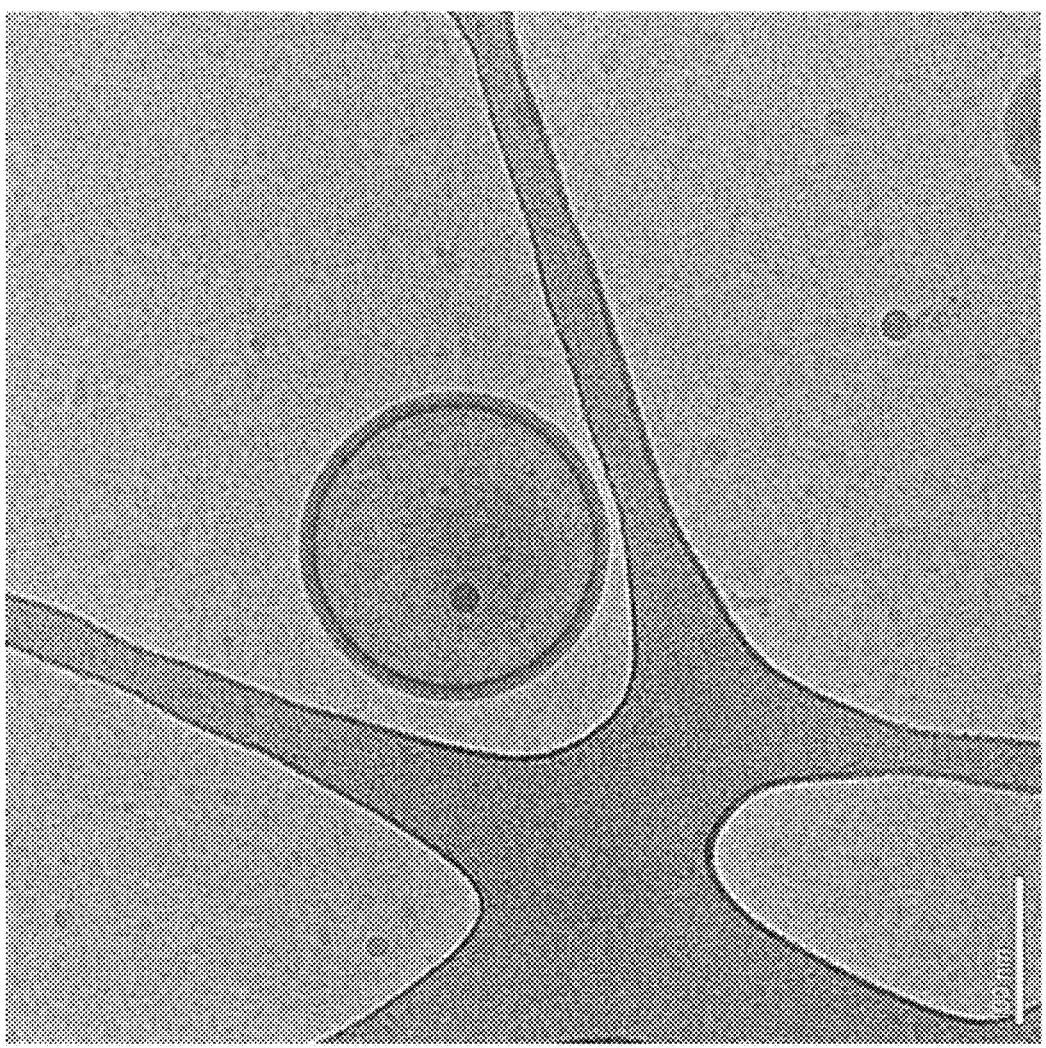
FIG. 6 depicts (a) CryoEM visualization of a fluorescently labelled cGAMP-loaded nanoparticle. (b) Confocal analysis and (c) flow-cytometric analysis show association of cGAMP with dead cells and debris following treatment with cGAMP-loaded nanoparticles.
Figure 6B:
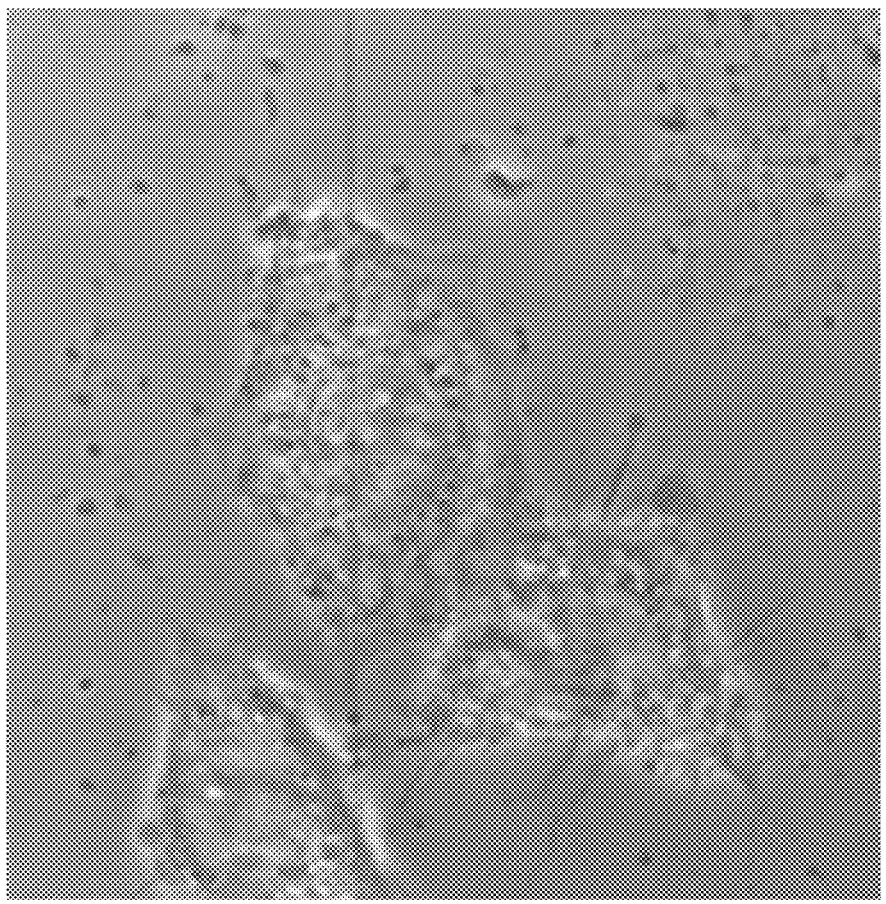
Figure 6C:
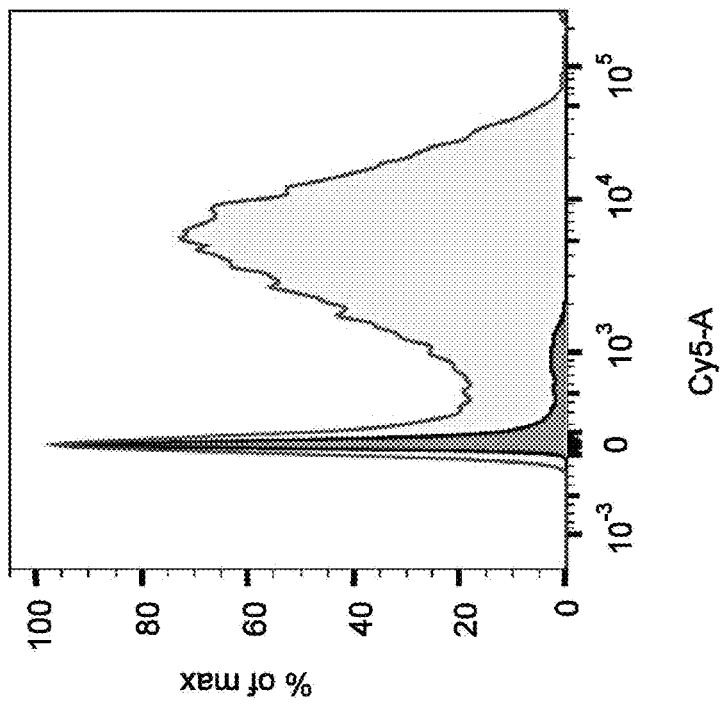

To demonstrate the treatment modality, HeLa cells were incubated with fluorescently labelled cGAMP-loaded nanoparticles (FIG. 6(a)). Upon intracellular uptake of the nanoparticles following 24 hr of incubation, the cells were allowed to vesiculate and generate cellular debris under the treatment of a chemotherapy drug, cisplatin as shown in FIG. 5. To demonstrate the association of the adjuvant nanoparticles with the cancer cell vesicles, the collected cellular debris were analyzed with confocal microscopy and quantified with fluorescence-activated cell sorting (FACS). The results show that the cellular debris contained a significant amount of adjuvant-loaded nanoparticles (FIG. 6(b), (c))

Figure 7:
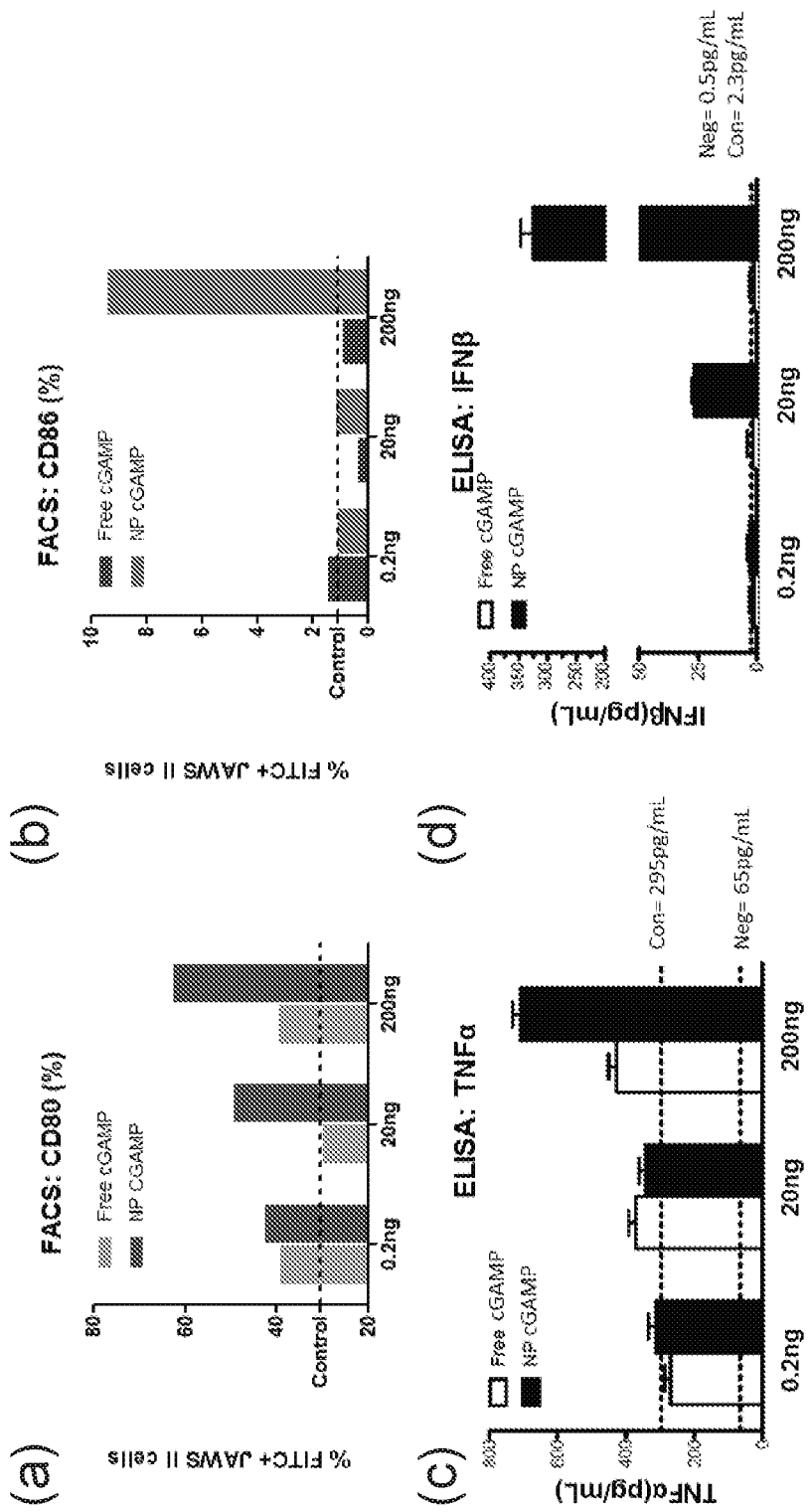
FIG. 7 depicts cellular debris generated by HeLa cells incubated with cGAMP nanoparticles were more immunogenic than those incubated with free cGAMP. The HeLa cell-associating cGAMP nanoparticles resulted in increased DC expression of CD80 (a), CD86 (b), and elevated DC secretion of TNF-α(c) and IFN-β(d)

The cancer cell debris were then collected and incubated with a JAWSII mouse dendritic cell (DC) line to examine their immunogenicity. HeLa cells incubated with either free cGAMP or cGAMP-loaded nanoparticles for 24 hr were treated with cisplatin, and the resulting cellular debris were collected to stimulate DCs. The DCs were collected after 24 hr of incubation and studied for DC activation markers CD86 and CD80. In vitro activation of DCs by immunogenic cellular debris was demonstrated by FACS analysis. The cytokine profile of the activated DCs was estimated by ELISA analysis for TNF-α and IFN-β. The results show that incubation with the cGAMP-loaded nanoparticles significantly increased the level of CD80 and CD86 and elevated the secretion of TNF-α and IFN-β by the DCs as compared to the free cGAMP, which has little capacity to associate with the cells (FIG. 7). In particular, IFN-β, a type-I IFN that is recognized as a crucial factor for shaping adaptive cellular immunity[7], is boosted by more than 100-fold with the adjuvant formulation.

Figure 8:
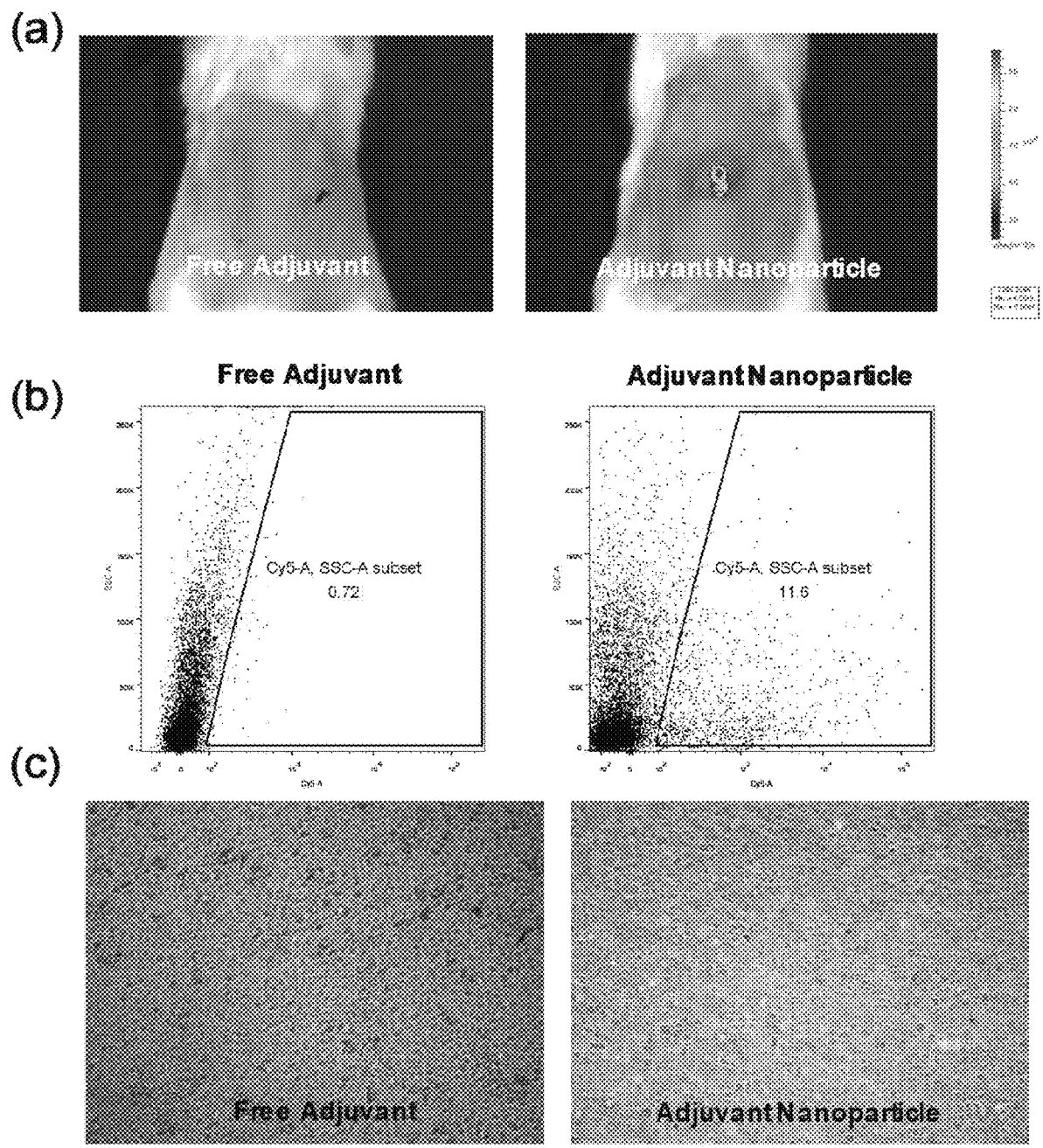
FIG. 8 depicts adjuvant retention with tumors and cancer cells were examined upon intratumoral injection of a dye-labelled STING agonist (red) in its free (Free Adjuvant) and nanoparticle form (Adjuvant Nanoparticle). 24 hours following the adjuvant administration the tumors and extracted cancer cells were examine by (a) whole-body imaging, (b) flow-cytometric analysis, and (c) fluorescence microscopy. The examinations demonstrate significant adjuvant retention inside the tumor and within cancer cells upon nanoparticle administration.

To validate cell-associating effect of the nanoparticle adjuvant formulation, B6 mice were inoculated subcutaneously with B16-OVA tumors. Nanoparticle-mediated adjuvant retention with the B16 cells was validated using whole body imaging, flow cytometric analysis, and fluorescence microscopy. Dye-labelled STING agonist (2'-[DY-547]-AHC-c-diGMP) was administered in its free form and nanoparticle form intra-tumorally and examined after 24 hours. It was observed that the nanoparticle formulation of the STING agonist was well retained inside the tumor (FIG. 8(a)). Upon cancer cell extraction from the dissected tumors, significant STING agonist association within the cancer cells was also confirmed from flow cytometry and confocal microscopy (FIG. 8(b), (c)). In contrast, little adjuvant retention either within the tumor or inside the cancer cells was observed upon free adjuvant administration.

Figure 9A:
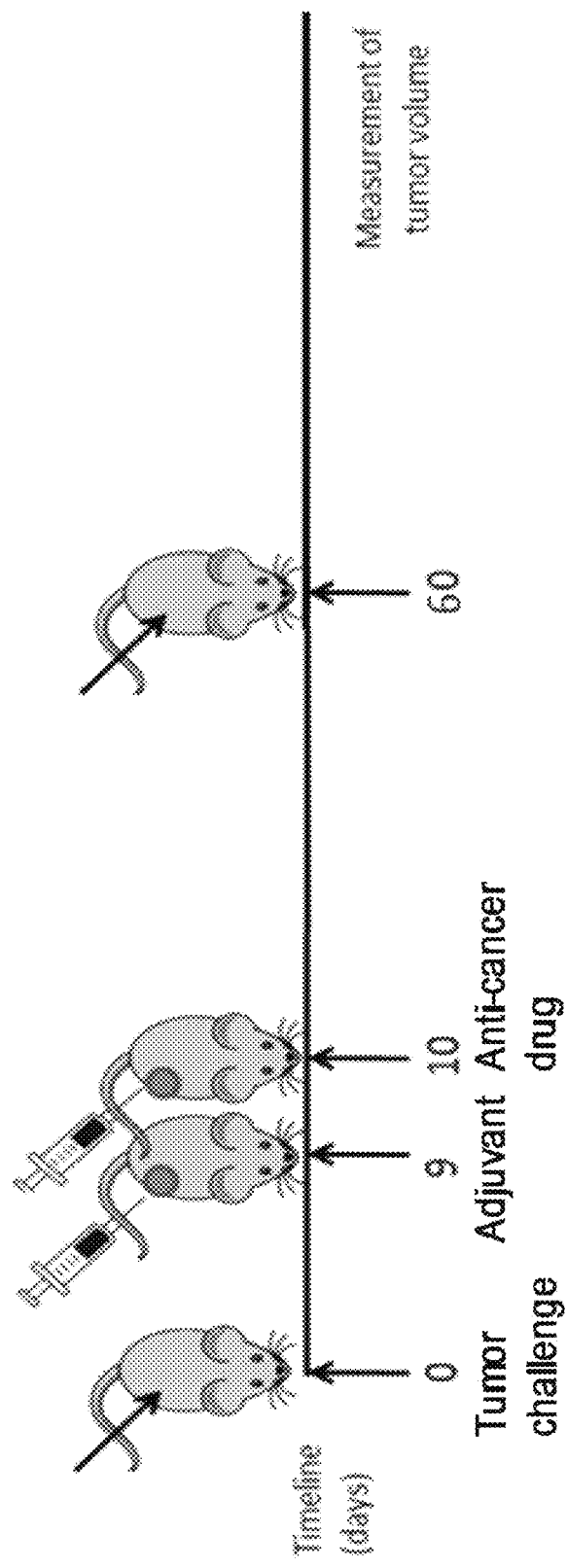
FIG. 9 depicts tumor treatment efficacy with different adjuvant and chemodrug combinations, including placebo, cisplatin only (CTTP only), cGAMP-loaded nanoparticle only (NP only), free cGAMP followed by cisplatin (cGAMP+CTTP), and cGAMP-loaded nanoparticle followed by cisplatin (NP+CTTP). (a) Tumor implantation and treatment regimen for B16-OVA murine melanoma subcutaneous model. (b) Tumor progression of all treatment groups over 60 days. (c) Survival analysis curve of the different treatment groups (n=9-11). (c) Comparison of mean tumor volume in a tumor rechallenge experiment with tumor-free surviving animals from the NP+CTTP group (n=4). The tumor growth was compared to a naïve control animal that was inoculated the same number of tumor cells (n=1).
Figure 9B:
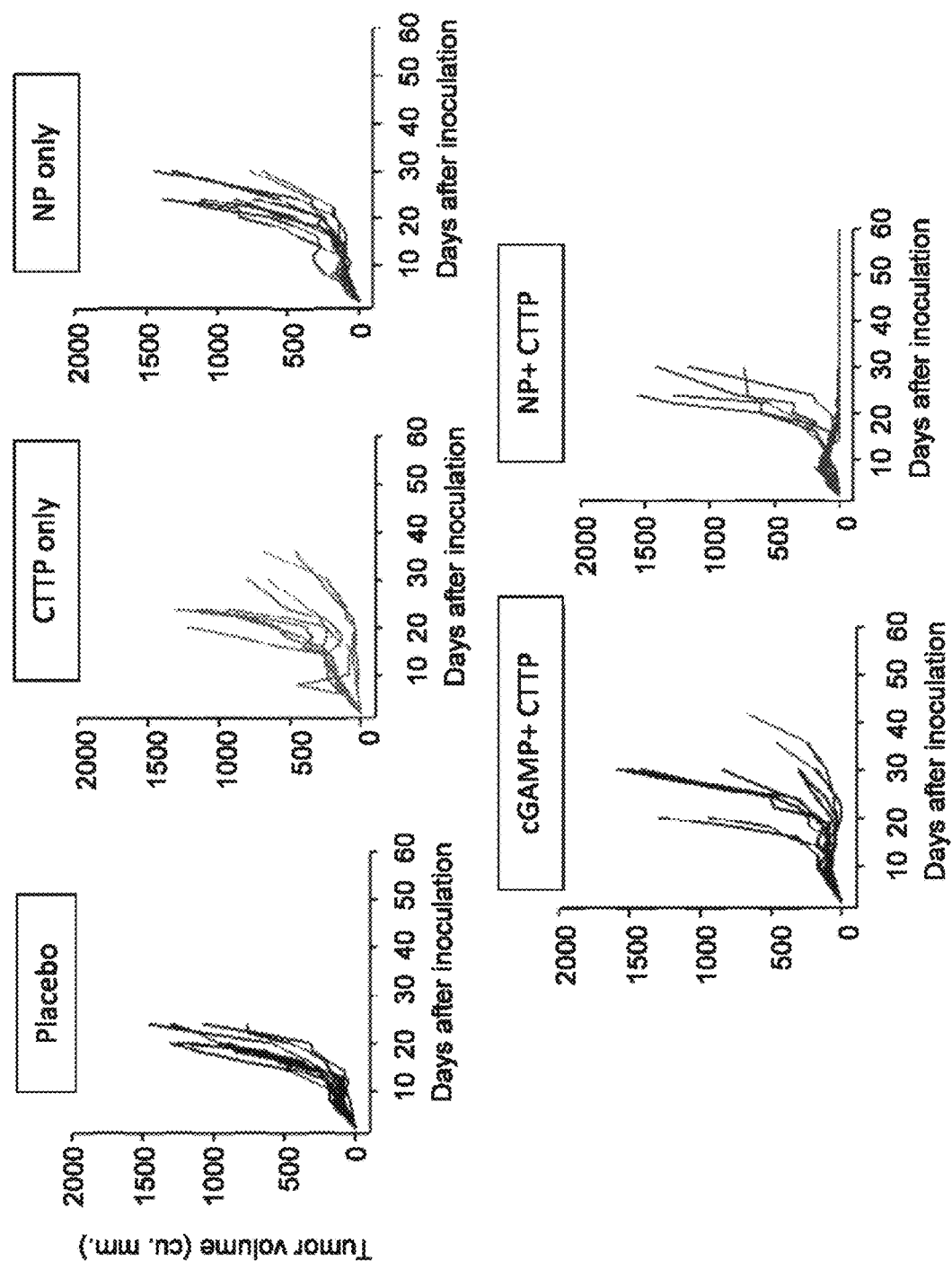
Figure 9C:
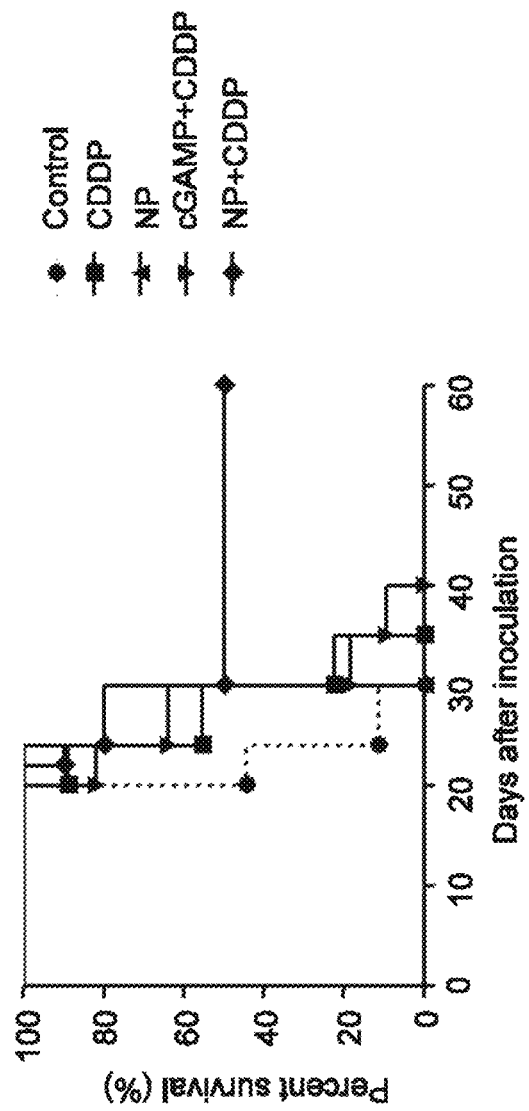
Figure 9D:
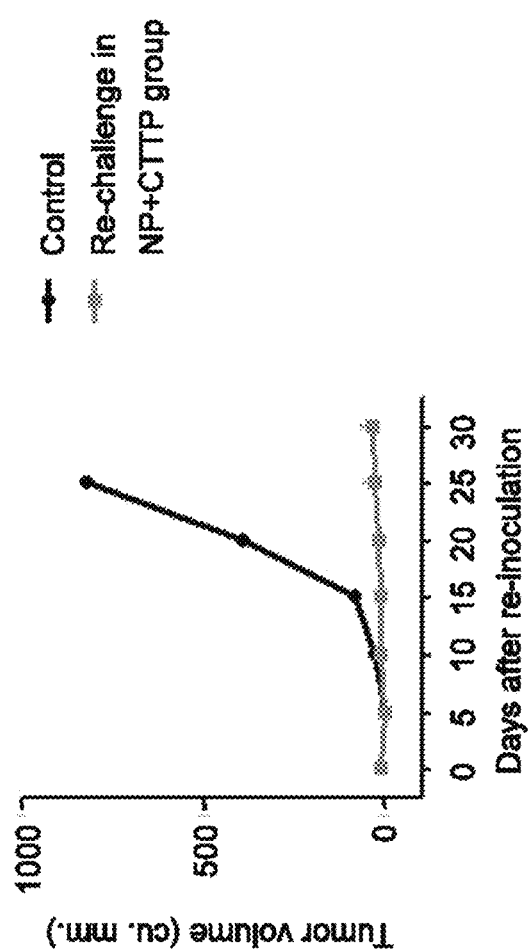

To study the in vivo efficiency of the treatment modality, B6 mice were inoculated subcutaneously with B16-OVA tumors. When the tumors appeared palpable, they were pre-treated with free cGAMP or cGAMP-loaded nanoparticles prior to chemotherapy by cisplatin (CTTP). 24 hours following intra-tumoral adjuvant administration, the mice were given an intra-tumoral cisplatin injection to induce cell death (FIG. 9(a)). These two groups are designated cGAMP+CTTP and NP+CTTP to differentiate the use of free cGAMP and cGAMP-loaded nanoparticles, respectively. For controls, tumor-bearing mice receiving no treatment (placebo), cistplatin only (CTTP only) and cGAMP-loaded nanoparticles only (NP only) were also prepared. For cGAMP administration, 2.5 µg of the adjuvant was administered in 50 µL of solution. For cisplatin administration, 235 µg of the chemodrug was administered in 100 µL of solution. Following the different treatments, the tumor volumes were monitored over time. In the NP+CTTP group, 50% of the animals (5 out of 10) showed complete tumor regression. In contrast, no other group had any tumor with complete regression (FIG. 9(b), (c)). Notably, neither CTTP only nor NP only treatment induced tumor regression, indicating that a synergistic effect was induced with their combination. In addition, none of the cGAMP+CTTP animals showed complete tumor regression, indicating that the synergistic effect in the NP+CTTP group was attributable to the enhanced adjuvant retention within the cancer cells. With the tumor-free surviving mice from the NP+CTTP group, 4 of them were re-challenged with B16-OVA cells on day 60 and compared to animals that had no prior tumor challenge and treatment. It was observed that the tumor growth was significantly reduced among the surviving animals from the NP+CTTP group, which indicate that these animals had acquired adaptive anti-cancer immunity (FIG. 9(d)). These results validate that by applying a cancer cell-associating immunologic adjuvant, the efficacy of a subsequent anticancer treatment can be significantly enhanced owing to the promotion of adaptive immunity.

In one embodiment of the present application, the immunologic adjuvant formulation comprises an adjuvant conjugated with a small molecule, a peptide, an antibody, an aptamer, a sugar moiety, a polymer or a combination thereof for recognizing and binding to a moiety on a cell surface. Preferably, the antibody comprises an immunoglobulin molecule, an Fv, a disulfide linked Fv, a monoclonal antibody, a scFv, a chimeric antibody, a single domain antibody, a CDR-grafted antibody, a diabody, a humanized antibody, a multispecific antibody, an Fab, a dual specific antibody, an Fab' fragment, a bispecific antibody, an F(ab')2 fragment, a bivalent fragment comprising two Fab fragments linked by a disulfide bridge at the hinge region; a Fd fragment consisting of the VH and CH1 domains; a Fv fragment consisting of the VL and VH domains of a single arm of an antibody, a dAb fragment, an isolated complementarity determining region (CDR), or a single chain antibody.

Figure 10:
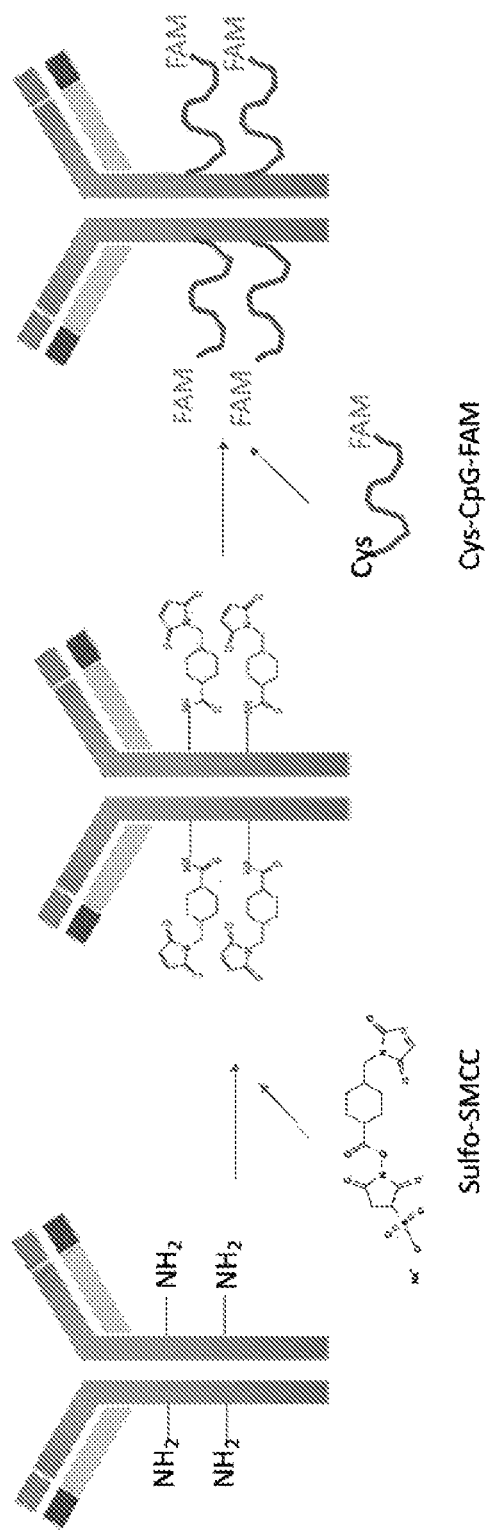
FIG. 10 depicts the preparation of antibody-conjugated CpG-ODN.

In one preferred embodiment, CpG-FAM was conjugated to antibodies for pathogenic cell association. Anti-CD44, which targets CD44 that are highly expressed on HeLa cells was adopted for adjuvant conjugation. 1 mg of the antibodies was first mixed with sulfo-SMCC at a molar ratio of 1:20 in 1×PBS for 24 h. Following the incubation, the functionalized antibodies were purified using a centrifugal filter with a molecular weight cut off (MWCO) of 30 kDa. The antibodies were then mixed with CpG-ODN containing a terminal cysteine group. A FAM dye was attached to the CpG-ODN for visualization (FIG. 10). Following 24 h of incubation, the CpG-conjugated antibodies were collected using a centrifugal filter with a MWCO of 30 kDa.

Figure 11:
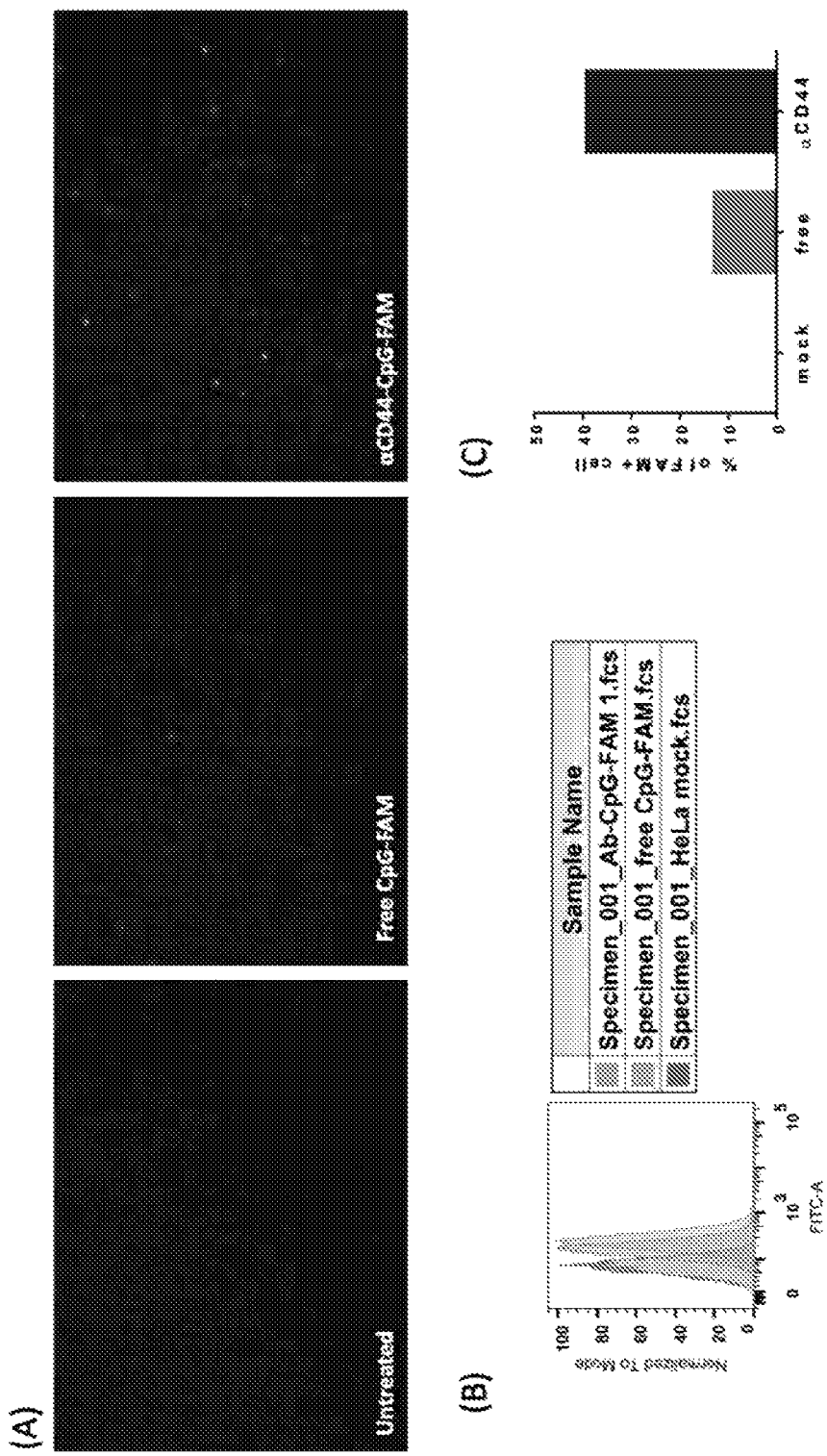
FIG. 11 depicts (A) Fluorescence microscopy observation of HeLa cellular monolayer following 3 h of incubation with free CpG-FAM (middle) and antibody-conjugated CpG-FAM (αCD44-CpG-FAM; right). Enhanced CpG association by the antibody-conjugated CpG-FAM was observed with a higher number of fluorescence punctates. (B) Flow cytometric analysis of cells with CpG-FAM. (C) Quantification of cells associated with CpG-FAM. Anti-CD44 conjugates (αCCD44) yielded higher CpG-FAM association on HeLa cells than free CpG-FAM (free).

We then assessed the CpG association to HeLa cells by incubating free CpG-FAM and anti-CD44-conjugated CpG-FAM with HeLa cells for 3 h. Following the incubation, the cells were washed and the CpG association was evaluated based on the FAM fluorescence. It was observed under fluorescence microscopy that the anti-CD44 CpG conjugates yielded higher fluorescence retention to the HeLa cell monolayer (FIG. 11A). Upon detaching the cells for flow cytometric analysis, enhanced CpG/cancer cell association was also observed with the anti-CD44 conjugates, demonstrating successful adjuvant targeting to the pathogenic cells (FIG. 11B, C).

Figure 12:
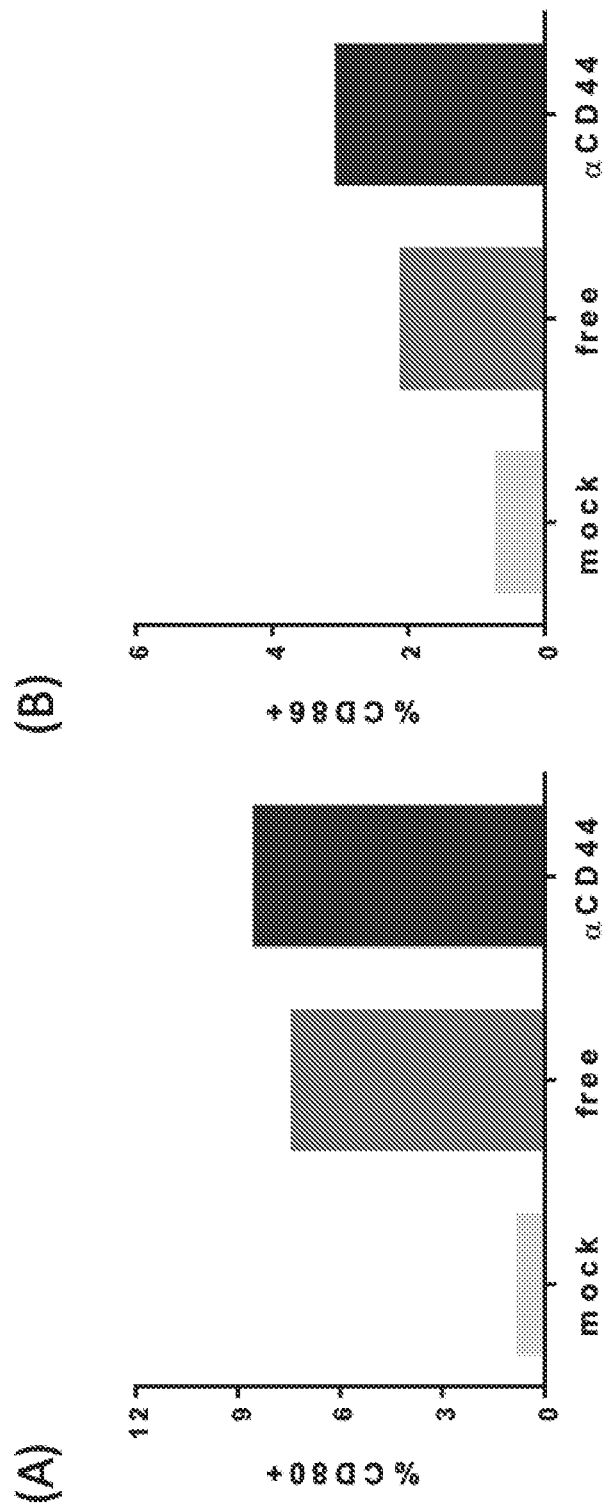
FIG. 12 depicts expression of maturation markers (A) CD80 and (B) CD86 by JAWSII cells following incubation with HeLa cell debris treated with free CpG (free) or anti-CD44 conjugated CpG (αCD44).

Following adjuvant association, the HeLa cells were then treated with a cytotoxic agent, doxorubicin, to induce cell death and generate cellular debris. Following 20 h of doxorubicin treatment, the cellular debris were collected and fed to JAWSII mouse dendritic cells. The JAWSII cells were then assessed for activation markers such as CD80 and CD86 after 20 hr of incubation with the cellular debris. It was observed that the debris of HeLa cells treated with anti-CD44 conjugated CpG triggered the highest levels maturation markers (FIG. 12).

Figure 13:
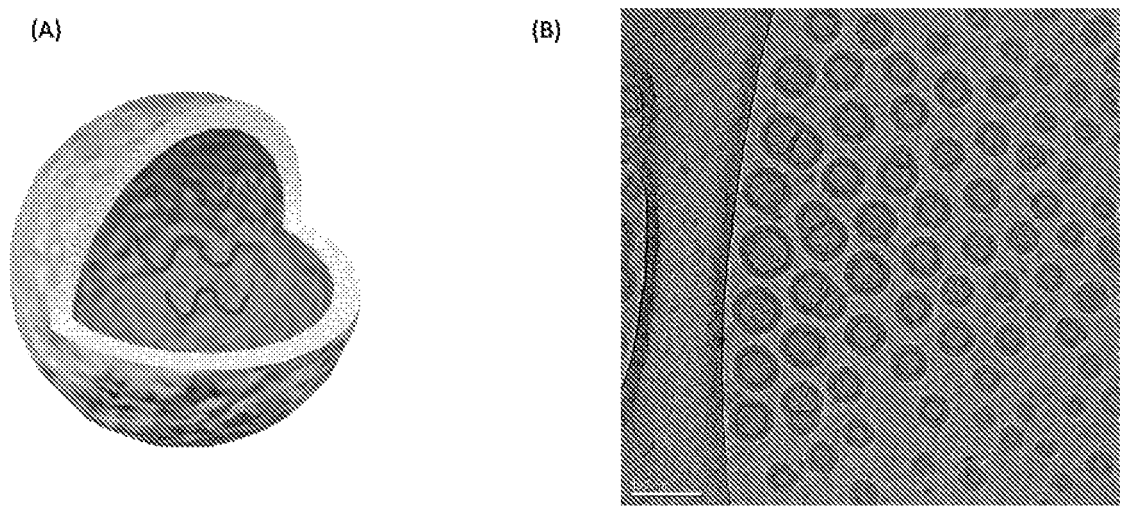
FIG. 13 depicts (A) Schematic presentation of nanoparticle-encapsulated CpG. (B) CryoEM visualization of nanoparticle-encapsulated CpG.

In another embodiment of the present application, CpG-FAM was encapsulated into polymeric nanoparticles for enhancing tumor cell uptake. A double emulsion process was employed to prepare the CpG-FAM loaded nanoparticles. 20 mg/mL of CpG was first dissolved in 50 µL of 100 mM of phosphate buffer, which was then emulsified in 500 µL of ethyl acetate containing 50 mg/mL of PLGA (10,000 Da, carboxyl-terminated, 50:50 lactide:glycolide). The resulting water-in-oil emulsion was then emulsified in 5 mL of 10 mM phosphate buffer. Following the incubation, the water-in-oil-in-water emulsion was then poured into 10 mL of 10 mM of phosphate buffer and the ethyl acetate was evaporated under nitrogen bombardment. After 1 h of solvent evaporation, the nanoparticle-encapsulated CpG was collected using a centrifugal filter with a MWCO of 30 kDa. Successful preparation of sub-100 nm nanoparticles containing CpG was verified using CryoEM (FIG. 13).

Figure 14:
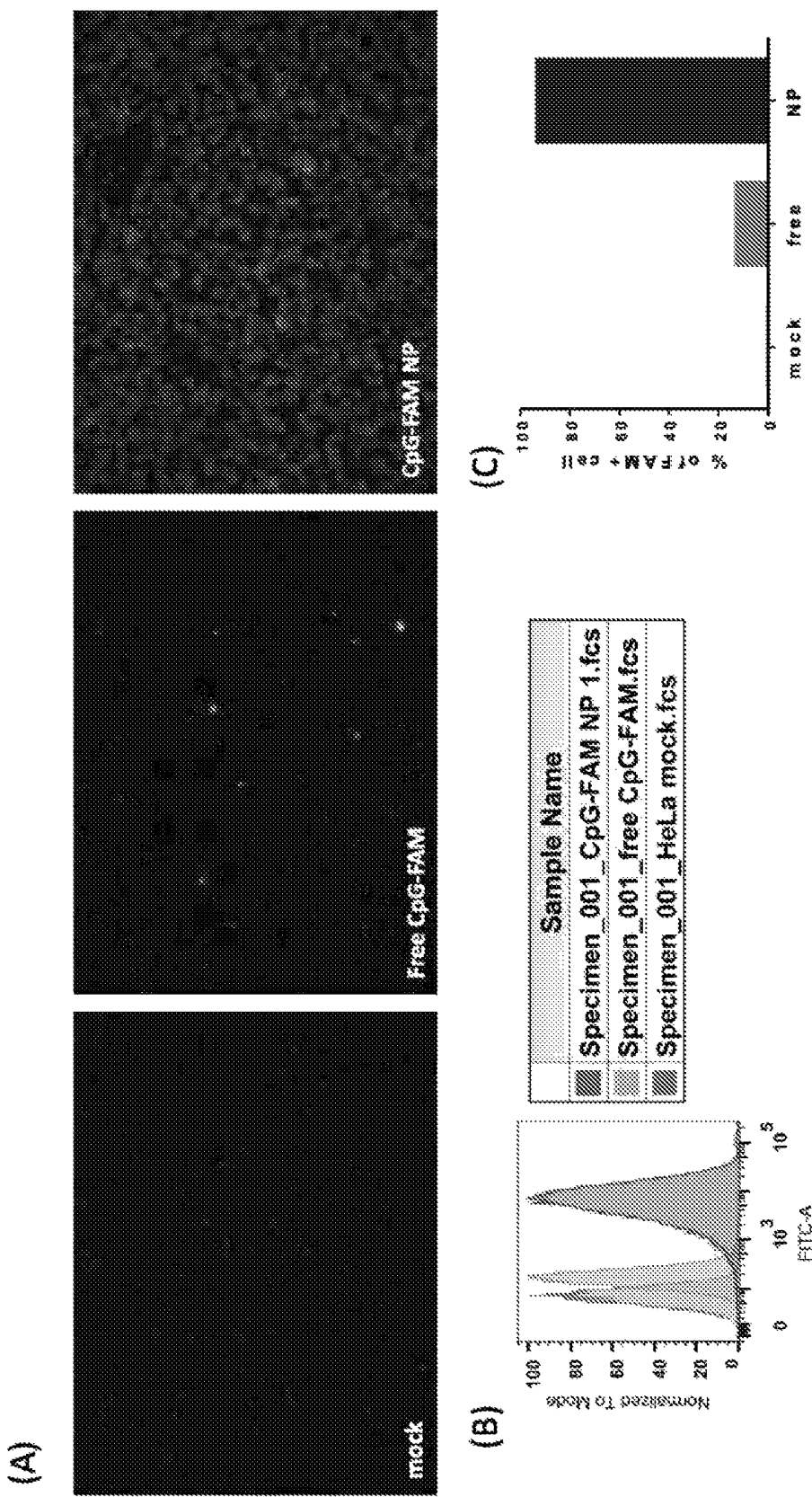
FIG. 14 depicts (A) Fluorescence microscopy observation of HeLa cellular monolayer following 24 h of incubation with free CpG-FAM (middle) and nanoparticle-encapsulated CpG (CpG-FAM NP; right). Enhanced CpG association was observed with a high number of fluorescence punctates. (B) Flow cytometric analysis of cells with CpG-FAM. (C) Quantification of cells associated with CpG-FAM. Anti-CD44 conjugates yielded higher CpG-FAM association on HeLa cells than free CpG-FAM.

We then assessed the CpG association to HeLa cells by incubating free CpG-FAM and nanoparticle-encapsulated CpG-FAM with HeLa cells for 24 h. Following the incubation, the cells were washed and the CpG association was evaluated based on the FAM fluorescence. It was observed under fluorescence microscopy that the nanoparticle-encapsulated CpG yielded higher fluorescence retention to the HeLa cell monolayer (FIG. 14A). Upon detaching the cells for flow cytometric analysis, enhanced CpG/cancer cell association was also observed with the nanoparticle-encapsulated CpG, demonstrating successful adjuvant targeting to the cells (FIG. 14B, C).

Figure 15:
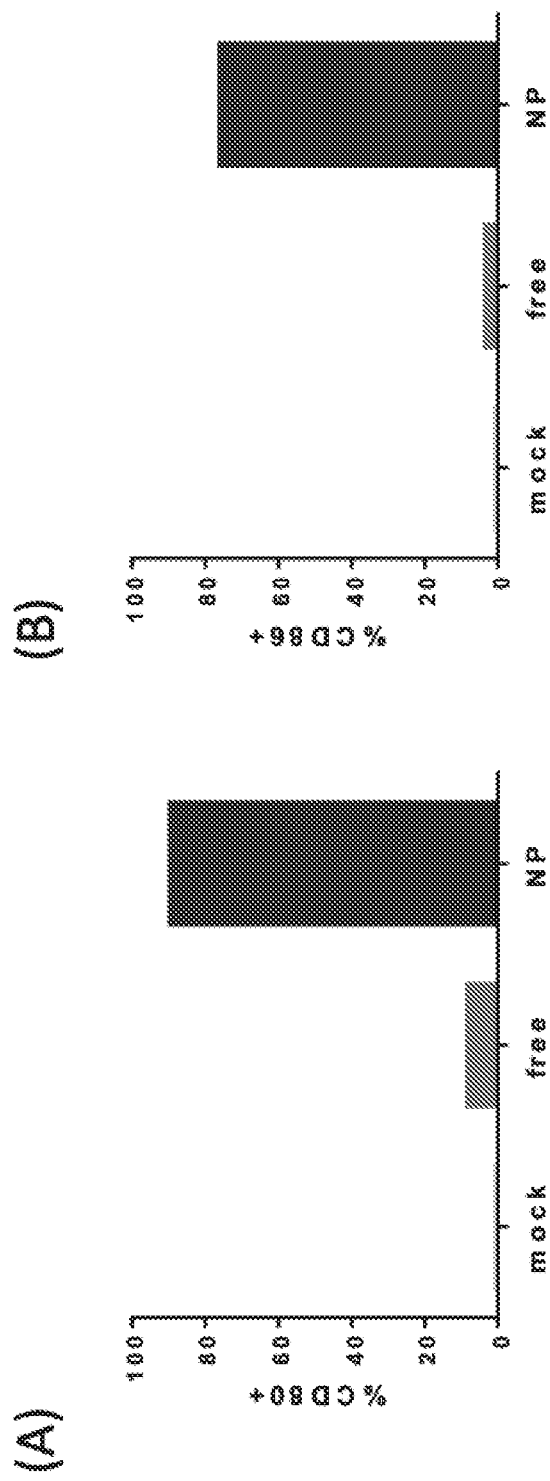
FIG. 15 depicts expression of maturation markers (A) CD80 and (B) CD86 by JAWSII cells following incubation with HeLa cell debris treated with free CpG (free) or nanoparticle-encapsulated CpG (NP).

Following adjuvant association, the HeLa cells were then treated with a cytotoxic agent, doxorubicin, to induce cell death and generate cellular debris. Following 20 h of doxorubicin treatment, the cellular debris were collected and fed to JAWSII mouse dendritic cells. The JAWSII cells were then assessed for activation markers such as CD80 and CD86 after 20 hr of incubation with the cellular debris. It was observed that the debris of HeLa cells treated with nanoparticle-encapsulated CpG triggered the highest levels maturation markers (FIG. 15).

In another embodiment of the present application, the means for inducing antigen release may be administered to the subject in need at the same time as the immunologic adjuvant formulation. Alternatively, the means for inducing antigen release may be administered to the subject in need before or after administration of the immunologic adjuvant formulation.

Figure 16:
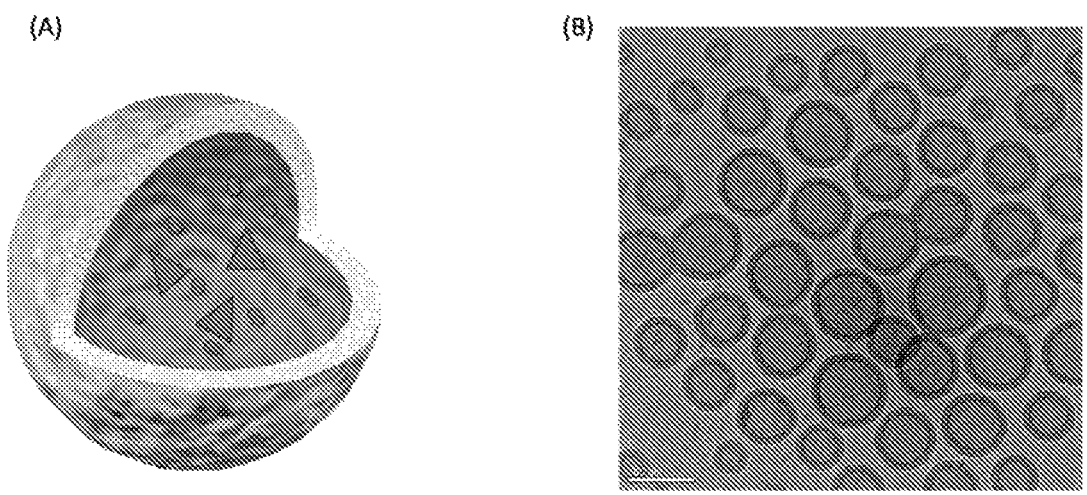
FIG. 16 depicts (A) Schematic presentation of a nanoparticle co-encapsulating a chemotherapeutic drug (daunorubicin) and an adjuvant (cd-GMP). (B) CryoEM visualization of nanoparticles co-encapsulating daunorubicin and cd-GMP.

In one embodiment, daunorubicin was encapsulated into nanoparticles along with cd-GMP STING agonist to simultaneously enable intracellular adjuvant delivery while triggering cell death. A double emulsion process was employed to prepare the nanoparticles co-encapsulating daunorubicin and cd-GMP. Solution containing 10 mg/mL of daunorubicin and 10 mg/mL of cd-GMP was first prepared with 100 mM of phosphate buffer, and 50 µL of the solution was emulsified in 500 µL of ethyl acetate containing 50 mg/mL of PLGA (10,000 Da, carboxyl-terminated, 50:50 lactide:glycolide). The resulting water-in-oil emulsion was then emulsified in 5 mL of 10 mM phosphate buffer. Following the incubation, the water-in-oil-in-water emulsion was then poured into 10 mL of 10 mM of phosphate buffer and the ethyl acetate was evaporated under nitrogen bombardment. After 1 h of solvent evaporation, the daunorubicin/cd-GMP nanoparticles were collected using a centrifugal filter with a MWCO of 30 kDa. As a control, nanoparticles encapsulating daunorubicin in the absence of cd-GMP was prepared with 20 mg/mL of daunorubicin as the inner aqueous phase. Successful preparation of sub-100 nm nanoparticles containing daunorubicin and cd-GMP was verified by cryoEM (FIG. 16).

Figure 17:
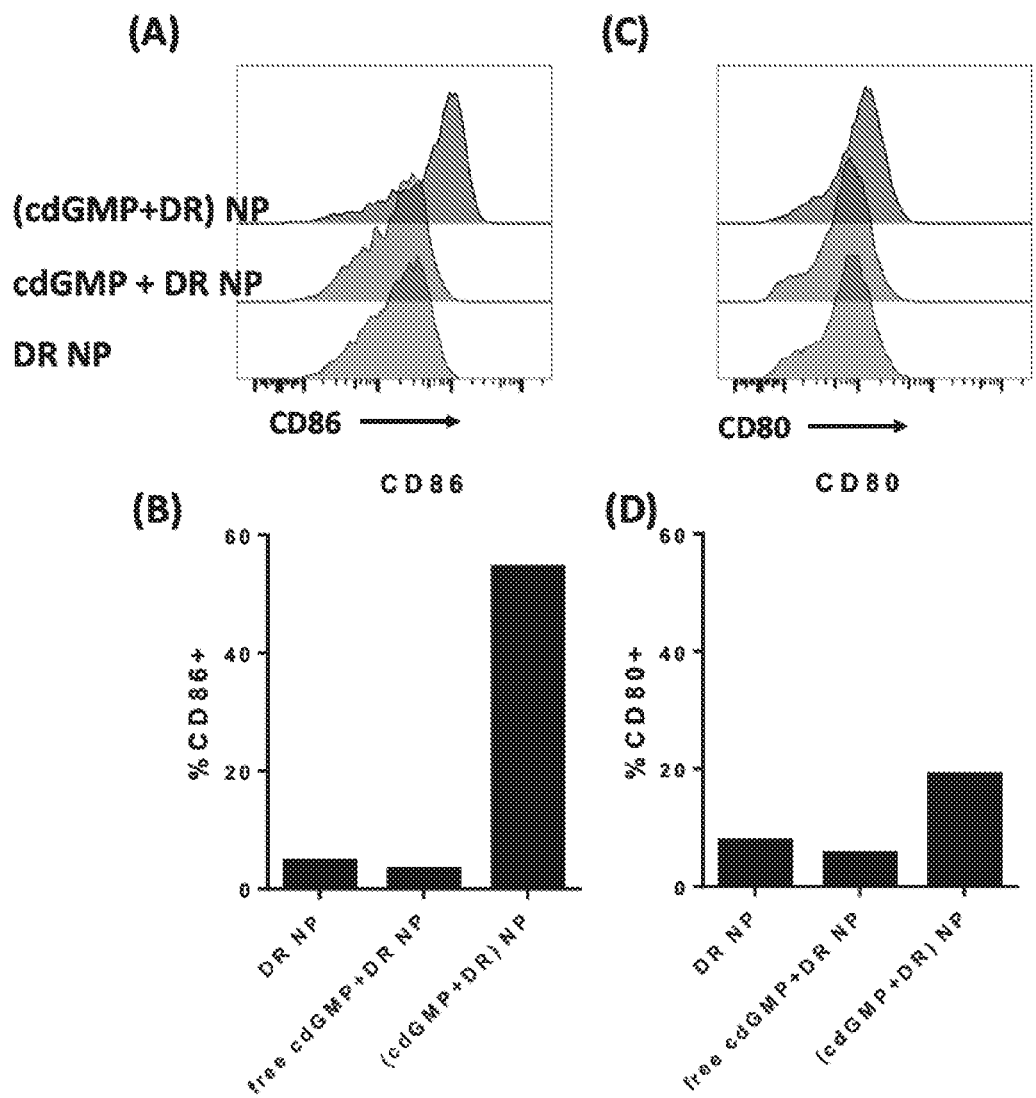
FIG. 17 depicts expression of maturation markers (A,B) CD86 and (C,D) CD80 by JAWSII cells following incubation with CT26 cell debris treated with nanoparticles coencapsulating daunorubicin and cd-GMP ((cdGMP+DR)NP), free cd-GMP and daunorubicin nanoparticles (cdGMP+DR NP) or daunorubicin nanoparticle only (DR NP).

We then treated CT26 colon cancer cells with three distinctive formulations: 1) daunorubicin nanoparticles only (DR NP); 2) free cd-GMP and daunorubicin nanoparticles (cd-GMP+DR NP); and 3) Nanoparticles co-encapsulating daunorubicin and cd-GMP ((cd-GMP+DR) NP. To 2 mL of CT26 culture were given 10 µg of daunorubicin and 10 µg of cd-GMP. Following 3 h of treatment, cellular debris was collected and fed to JAWSII mouse dendritic cells. The JAWSII cells were then assessed for activation markers such as CD80 and CD86 after 24 hr of incubation with the cellular debris. It was observed that the debris of CT26 cells treated with nanoparticles co-encapsulating daunorubicin and cd-GMP triggered the highest levels maturation markers such as CD80 and CD86 (FIG. 17).

Figure 18:
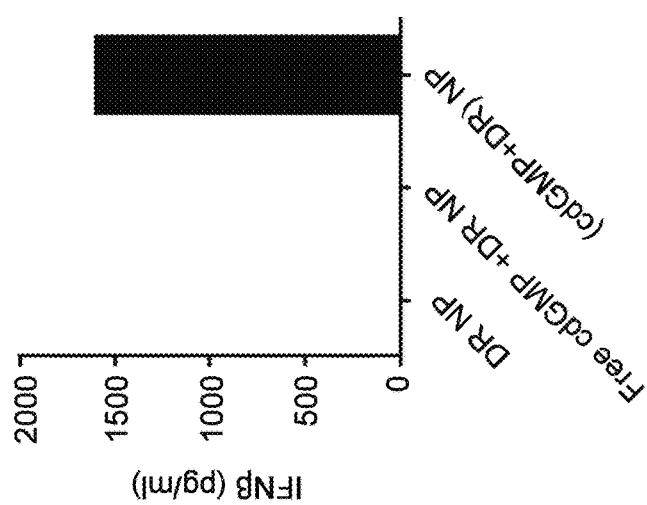
FIG. 18 depicts secretion of IFN-β from JAWSII cells following incubation with CT26 cell debris treated with nanoparticles coencapsulating daunorubicin and cd-GMP ((cdGMP+DR)NP), free cd-GMP and daunorubicin nanoparticles or daunorubicin nanoparticle only (DR NP).

The supernatants from the JAWSII cells were also assessed for IFN-β, which is a major lymphocyte activation signal for T cell activation and expansion. It was observed that the debris of CT26 cells treated with nanoparticles co-encapsulating daunorubicin and cd-GMP induced the highest level IFN-β production in JAWSII cell (FIG. 18). These results demonstrate the adjuvant formulation co-delivering cytotoxic agents and immunologic adjuvants to cells can induce cellular debris with significant immunogenicity.

In summary, the description above demonstrates that the treatment kit comprising immunologic adjuvant formulation is capable of facilitating immune response target specific cells. A novel treatment modality was also demonstrated based on the cell-associating immunologic adjuvant, which is capable of enhancing adaptive immunity to the diseased cell. The method and the treatment kit are applicable to any existing treatments that induce release of cellular debris and antigens, including but not limited to chemotherapy, radiation therapy, photothermal therapy, immunotherapy, and surgical interventions. Other approaches for associating immunologic adjuvants with pathogenic cells, including but not limited to methods that facilitate intracellular entry, membrane tethering, and surface binding of immunologic adjuvants, are also contemplated. The immunologic adjuvants can also include but not limited to MPLA, CpG, poly(I:C), variants of cyclic-dinucleotides, and other immune-stimulatory molecules. Treatment kit that contain both immunologic adjuvant formulation and means for inducing antigen release, such as nanoparticles containing both cGAMP and chemodrugs, for cell association are also contemplated.

It will be apparent to those skilled in the art that various modifications and variations can be made to the disclosed embodiments. It is intended that the specification and examples be considered as exemplary only, with a true scope of the disclosure being indicated by the following claims and their equivalents.

REFERENCES

The references listed below and referred to herein are hereby incorporated into this specification by reference unless this specification expressly provides otherwise.

1. Bachmann, M. F. and G. T. Jennings, Vaccine delivery: a matter of size, geometry, kinetics and molecular patterns. Nat Rev Immunol, 2010. 10(11): p. 787-96.
2. Ott, P. A., et al., An immunogenic personal neoantigen vaccine for patients with melanoma. Nature, 2017. 547 (7662): p. 217-+.
3. Fan, Y., et al., Immunogenic Cell Death Amplified by Co-localized Adjuvant Delivery for Cancer Immunotherapy. Nano Lett, 2017.
4. Fu, J., et al., STING agonist formulated cancer vaccines can cure established tumors resistant to PD-1 blockade. Sci Transl Med, 2015. 7(283): p. 283ra52.
5. Galluzzi, L, et al., Immunogenic cell death in cancer and infectious disease. Nat Rev Immunol, 2017. 17(2): p. 97-111.
6. Fridman, W. H., et al., The immune contexture in human tumours: impact on clinical outcome. Nat Rev Cancer, 2012. 12(4): p. 298-306.
7. Hertzog, P. J., Overview. Type I interferons as primers, activators and inhibitors of innate and adaptive immune responses. Immunology and Cell Biology, 2012. 90(5): p. 471-473.

What is claimed is:

1. A treatment with cells; and
   composition comprising a polymeric nanoparticle, wherein the polymeric nanoparticle comprises:
   a solid polymeric shell impermeable to water, and
   one or more aqueous cores enclosed by the polymeric shell, and
   wherein the polymeric nanoparticle co-encapsulates daunorubicin and cyclic di-GMP.

2. The composition of claim 1, wherein the polymeric shell has a thickness less than 25 nm and the polymeric nanoparticle has an outer diameter of 30-600 nm.

3. The treatment kit composition of claim 1, wherein the further comprising an antibody, an aptamer, a sugar moiety, a polymer or a combination thereof for recognizing and binding to a moiety on a cell surface.

4. The composition of claim 3, wherein the antibody is an immunoglobulin molecule, an Fv, a disulfide linked Fv, a monoclonal antibody, a scFv, a chimeric antibody, a single domain antibody, a CDR-grafted antibody, a diabody, a humanized antibody, a multispecific antibody, an Fab, a dual specific antibody, an Fab' fragment, a bispecific antibody, an F(ab')2 fragment, a bivalent fragment comprising two Fab fragments linked by a disulfide bridge at the hinge region; a Fd fragment consisting of the VH and CH1 domains; a Fv fragment consisting of the VL and VH domains of a single arm of an antibody, a dAb fragment, an isolated complementarity determining region (CDR), or a single chain antibody.

5. The composition of claim 1, further comprising a molecule capable of tethering to a cell membrane.

6. The composition of claim 5, wherein the molecule capable of tethering to a cell membrane is lipophilic or amphiphilic.

7. The composition of claim 6, wherein the lipophilic molecule comprises fatty acid chains, cholesterol, or phospholipids.

8. The composition of claim 6, wherein the amphiphilic molecule comprises lipid-PEG conjugates.

9. The composition of claim 1, further comprising cell penetrating peptides for intracellular delivery.

10. The composition of claim 9, wherein the cell penetrating peptides comprise HIV-1 TAT peptide (GRKKRRQRRRPPQ, SEQ ID NO: 1), penetratin (RQIKIWFQNRRMKWKK, SEQ ID NO: 2), polyarginines (Rn, SEQ ID NO: 3), or transportan (GWTLNSAGYLLGINLKALAALAKKIL, SEQ ID NO: 4).

11. A method of treating-a-disease cancer in a subject in need thereof, comprising:
    administering the composition of claim 1 to a subject suffering from cancer.

12. The method of claim 11, wherein the administered composition further comprises an antibody which is an immunoglobulin molecule, an Fv, a disulfide linked Fv, a monoclonal antibody, a scFv, a chimeric antibody, a single domain antibody, a CDR-grafted antibody, a diabody, a humanized antibody, a multispecific antibody, an Fab, a dual specific antibody, an Fab' fragment, a bispecific antibody, an F(ab')2 fragment, a bivalent fragment comprising two Fab fragments linked by a disulfide bridge at the hinge region; a Fd fragment consisting of the VH and CH1 domains; a Fv fragment consisting of the VL and VH domains of a single arm of an antibody, a dAb fragment, an isolated complementarity determining region (CDR), or a single chain antibody.

13. The method of claim 11,
    wherein the administered polymeric nanoparticle further comprises a molecule capable of tethering to a cell membrane.

14. The method of claim 13, wherein the molecule is lipophilic or amphiphilic.

15. The method of claim 14, wherein the lipophilic molecule comprises fatty acid chains, cholesterol, or phospholipids.

16. The method of claim 14, wherein the amphiphilic molecule comprises lipid-PEG conjugates.

17. The method of claim 11, further comprising:
wherein the nanoparticle further comprises cell penetrating peptides for intracellular delivery.

18. The method of claim 17, wherein the cell penetrating peptides comprise HIV-1 TAT peptide (GRKKRRORRRPPQ, SEQ ID NO: 1), penetratin (RQIKIWFQNRRMKWKK, SEQ ID NO: 2), polyarginines (Rn, SEQ ID NO: 3), or transportan (GWTLNSAGYLLGINLKALAALAKKIL, SEQ ID NO: 4).

19. The method of claim 11, wherein administering to the subject is by at least one mode selected from the group consisting of parenteral, subcutaneous, intramuscular, intravenous, intra-articular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, and transdermal.

\* \* \* \* \*